United States Patent
Grimes et al.

(10) Patent No.: US 6,592,547 B2
(45) Date of Patent: *Jul. 15, 2003

(54) METHODS AND DEVICES FOR OCCLUDING THE ASCENDING AORTA AND MAINTAINING CIRCULATION OF OXYGENATED BLOOD IN THE PATIENT WHEN THE PATIENT'S HEART IS ARRESTED

(76) Inventors: Kevin V. Grimes, 1464 Gilmore St., Mountain View, CA (US) 94040; Jan Komtebedde, 1065 Merriman Rd., Cupertino, CA (US) 95045; Daniel C. Rosenman, 1415 Waller St. #3, San Francisco, CA (US) 94117; Hanson S. Gifford, III, 3180 Woodside Rd., Woodside, CA (US) 94062; Michi E. Garrison, 212 Roosevelt Blvd., Half Moon Bay, CA (US) 94019; Wesley D. Sterman, 2121 Sacramento St. #604, San Francisco, CA (US) 94109; David M. Taylor, 38396 Redwood Ter., Fremont, CA (US) 94536; A. Adam Sharkawy, 731 Canyon Rd., Redwood City, CA (US) 94062; Pinaki Ray, 4747 Mendocino Ter., Fremont, CA (US) 94555

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 90 days.

(21) Appl. No.: 09/235,043

(22) Filed: Jan. 21, 1999

(65) Prior Publication Data

US 2001/0056260 A1 Dec. 27, 2001

Related U.S. Application Data

(63) Continuation-in-part of application No. 09/012,833, filed on Jan. 23, 1998, now Pat. No. 6,159,178.

(51) Int. Cl.[7] ............................................. A61M 29/00
(52) U.S. Cl. .................................................. 604/96.01
(58) Field of Search ........................ 604/96.01, 102.01, 604/102.02, 102.03, 103.09, 101.01, 101.02, 101.04

(56) References Cited

U.S. PATENT DOCUMENTS 5,217,466 A * 6/1993 Hasson ........................ 606/119
5,364,347 A * 11/1994 Jang ............................. 604/53

(List continued on next page.)

FOREIGN PATENT DOCUMENTS

| EP | 0357338 | 3/1990 |
| EP | 0604803 | 7/1994 |
| WO | WO 9630072 | 10/1996 |

OTHER PUBLICATIONS

U.S. patent application Ser. No. 08/782,113, Heartport, Inc.

Primary Examiner—Sharon Kennedy

(57) ABSTRACT

A method and device for occluding a patient's ascending aorta, maintaining circulation of oxygenated blood in the patient and delivering cardioplegic fluid to arrest the patient's heart. An aortic occlusion catheter has an occluding member for occluding the ascending aorta. The aortic occlusion catheter passes through a cannula. Delivery of oxygenated blood is accomplished through either the cannula or the aortic occlusion catheter. In another aspect of the invention, an arterial cannula having a curved or angled distal portion. An introducer straightens the distal portion for introduction into the patient. In still another aspect of the invention, an open-mesh stabilizer is used to stabilize a discoid occluding member.

6 Claims, 23 Drawing Sheets

U.S. PATENT DOCUMENTS

| | | |
|---|---|---|
| 5,425,708 A | 6/1995 | Nasu |
| 5,484,803 A | 1/1996 | Richter |
| RE35,352 E | 10/1996 | Peters |
| 5,584,803 A | 12/1996 | Stevens et al. |
| 5,682,906 A | 11/1997 | Sterman |
| 5,863,366 A | 1/1999 | Snow |
| 5,913,842 A * | 6/1999 | Boyd et al. .................... 604/28 |
| 6,021,340 A * | 2/2000 | Randolph et al. ........... 600/381 |
| 6,027,476 A * | 2/2000 | Sterman et al. ................ 604/96 |
| 6,217,548 B1 * | 4/2001 | Tsugita et al. ........... 604/96.01 |

* cited by examiner

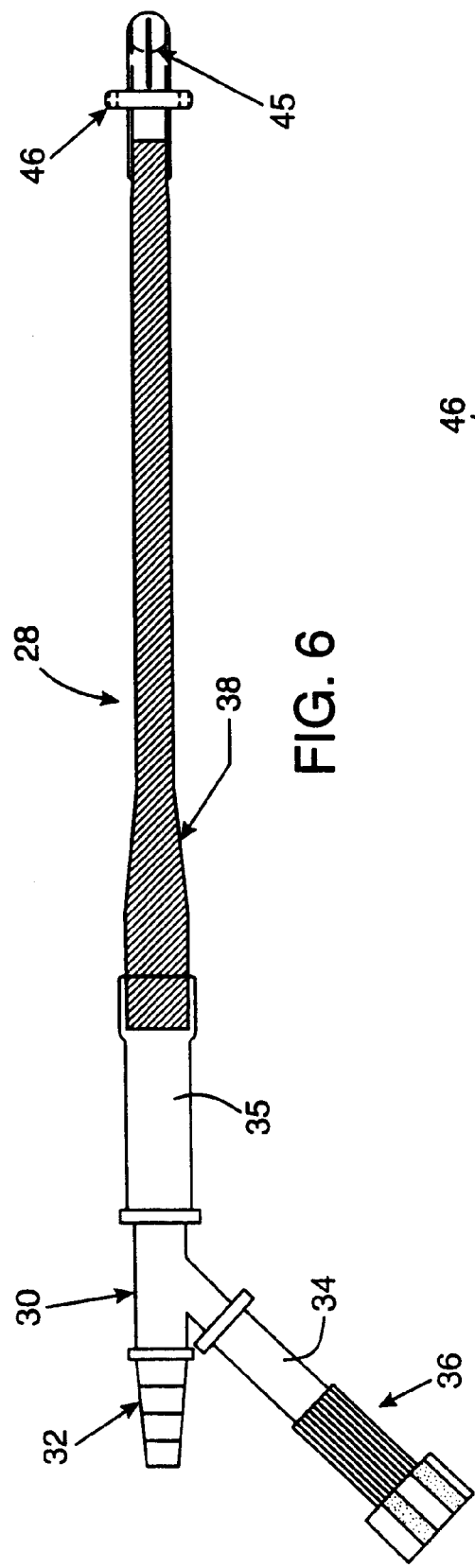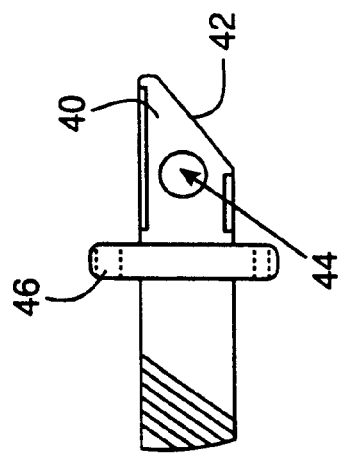
FIG. 6
FIG. 7

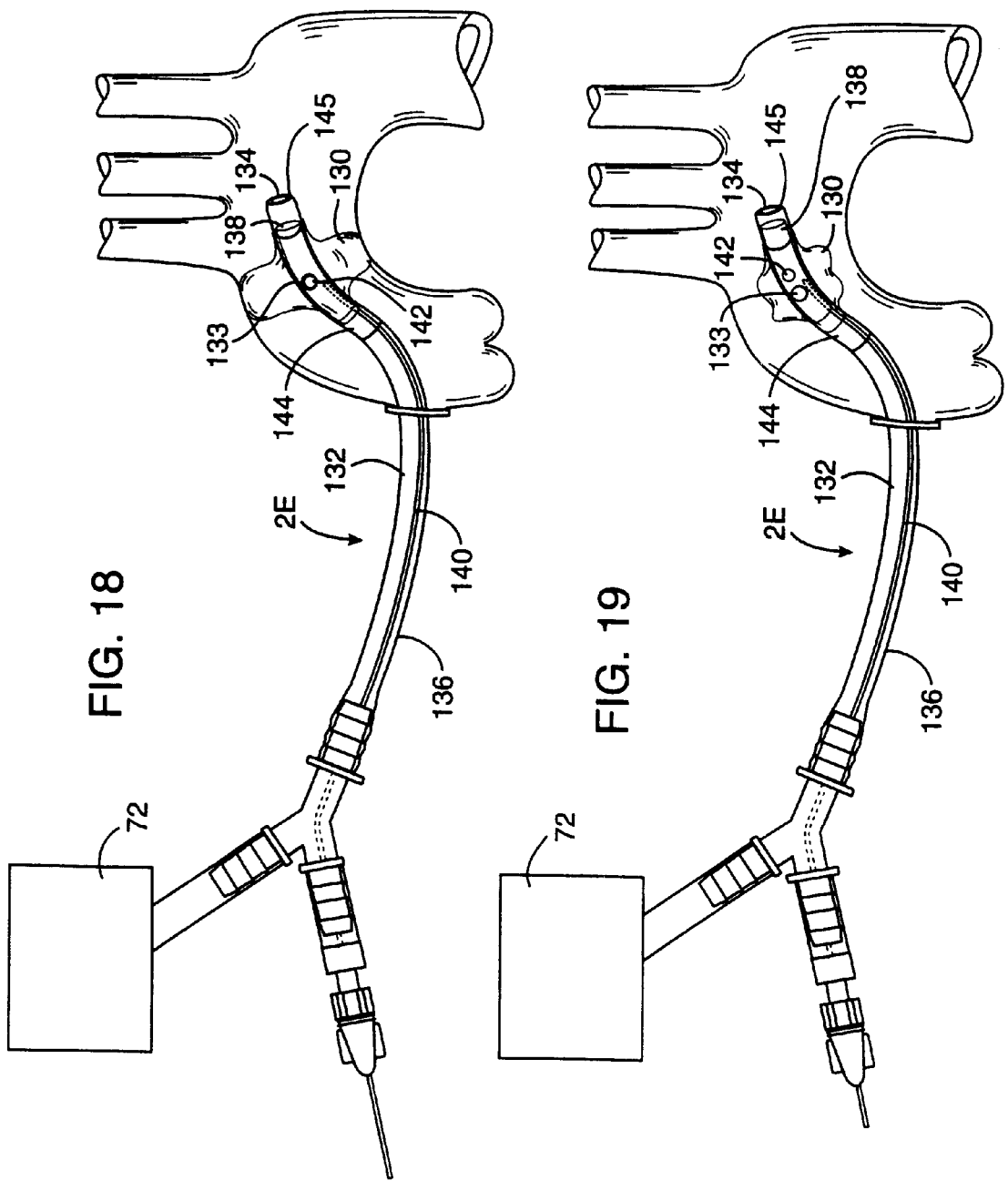

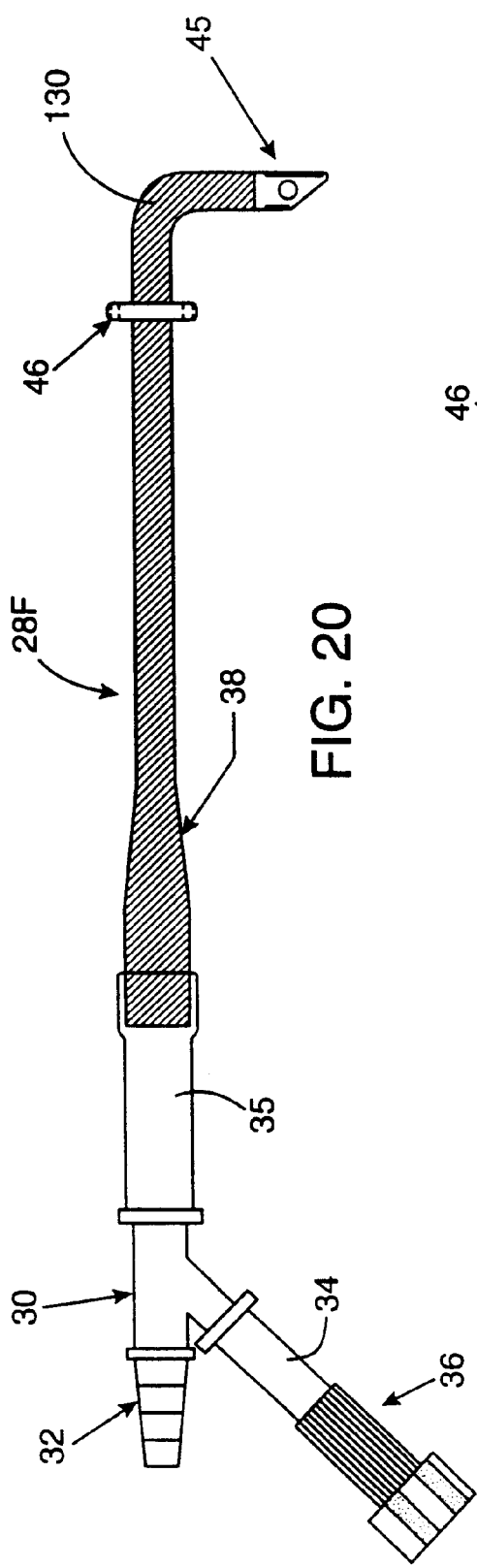
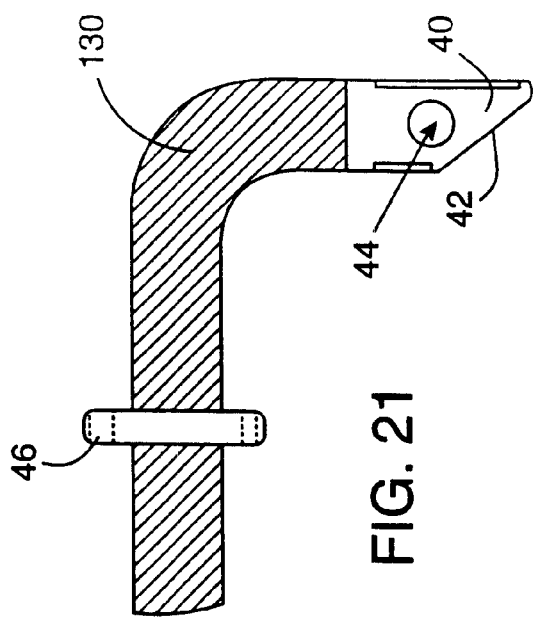

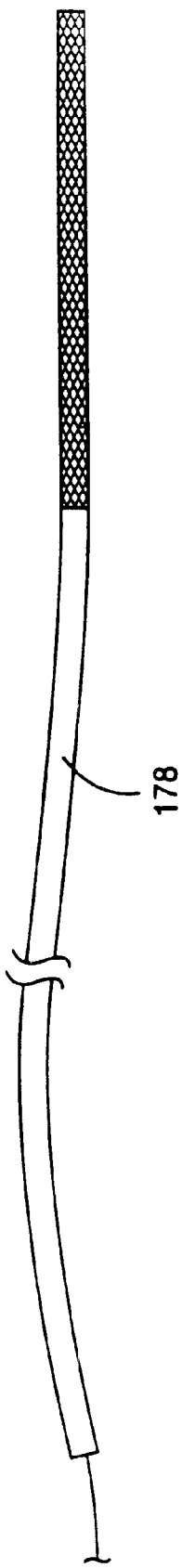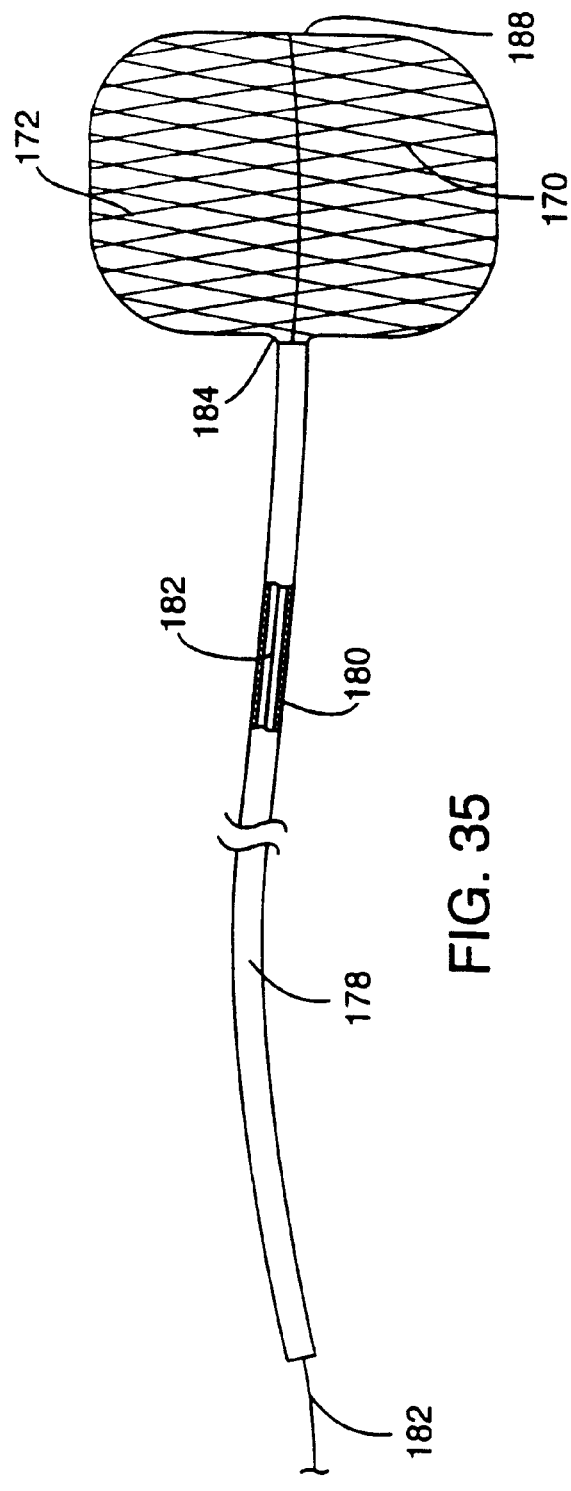

US 6,592,547 B2

METHODS AND DEVICES FOR OCCLUDING THE ASCENDING AORTA AND MAINTAINING CIRCULATION OF OXYGENATED BLOOD IN THE PATIENT WHEN THE PATIENT'S HEART IS ARRESTED

CROSS-REFERENCE TO RELATED APPLICATIONS

This application is a continuation-in-part of U.S. patent application Ser. No. 09/012,833, filed Jan. 23, 1998, now U.S. Pat. No. 6,159,178, issued Dec. 12, 2000, which is incorporated herein by reference.

BACKGROUND OF THE INVENTION

The present invention is directed to methods and devices for occluding a patient's ascending aorta and maintaining circulation of oxygenated blood in the patient when the patient's heart is arrested. Such devices and methods are useful for performing various procedures on a patient's vascular system and heart such as the procedures described in U.S. Pat. Nos. 5,584,803 and 5,682,906 which describe coronary artery bypass grafting (CABG) and valve procedures, respectively. Another device and method for occluding a patient's ascending aorta is described in U.S. Pat. No. Re. 35,352.

The methods and devices described in the above-mentioned patents use an internal occlusion device to occlude the ascending aorta rather than a conventional external cross-clamp. Use of an internal occlusion device may reduce strokes as compared to conventional external cross-clamps since external cross-clamps distort and compress the aorta which may release emboli leading to strokes.

It is an object of the invention to provide alternative methods and devices for occluding a patient's ascending aorta and maintaining circulation of oxygenated blood when the patient's heart is arrested.

SUMMARY OF THE INVENTION

In accordance with the object of the invention, the present invention provides alternative methods and devices for occluding a patient's ascending aorta and maintaining circulation of oxygenated blood in a patient when the patient's heart is arrested.

In a first preferred method and device of the present invention, an aortic occlusion device having a blood delivery lumen and an occluding member is introduced into the patient's aortic arch. The occluding member has an interior in fluid communication with the blood delivery lumen so that delivery of oxygenated blood inflates the occluding member. An advantage of this method is that a separate inflation lumen is not necessary. The aortic occlusion device preferably passes through a cannula having a y-arm with the aortic occlusion catheter passing through an arm of the y-arm. The other arm of the y-arm connector is coupled to the source of oxygenated blood so that bypass support can be maintained even when the aortic occlusion device has been removed.

In another preferred method and device, oxygenated blood is delivered to the patient through the aortic occlusion catheter. The aortic occlusion catheter also passes through a cannula with a y-arm connector so that bypass support can be maintained when the aortic occlusion device is removed. The aortic occlusion device also preferably includes a lumen for delivering cardioplegic fluid and venting the ascending aorta and a pressure lumen for measuring pressure in the ascending aorta. If the lumens are not provided in the aortic occlusion device, delivery of cardioplegic fluid, venting of the ascending aorta and pressure monitoring may be accomplished with the cannula.

In another preferred device, the aortic occlusion device has an occluding member mounted to a side of the catheter. The occluding member has a pathway therethrough which is in communication with a lumen in the aortic occlusion catheter. The pathway directs cardioplegic fluid toward the coronary ostia while the aortic occlusion device directs the oxygenated blood in the direction of normal blood flow in the aorta.

In another aspect of the invention, the cannula has a curved or angled distal end. The distal end is straightened for introduction by the introducer.

In still another aspect of the present invention, the occluding member is stabilized by a mesh structure to prevent distortion of the occluding member.

These and other aspects and advantages of the present invention will become apparent from the following description and drawings.

BRIEF DESCRIPTION OF THE DRAWINGS

FIG. 6 shows a cannula;

FIG. 7 shows an enlarged view of the distal end of the cannula of FIG. 6;

FIG. 18 shows another preferred aortic occlusion device with the balloon occluding the ascending aorta; and FIG. 19 shows the aortic occlusion device of FIG. 18 with the balloon deflated.

FIG. 20 shows a cannula having an angled or curved distal portion;

FIG. 21 shows the distal portion of the cannula of FIG. 20;

FIG. 34 shows the stabilizer of FIG. 33 in a collapsed position; and

FIG. 35 shows the stabilizer of FIG. 33 in an expanded position.

DESCRIPTION OF THE PREFERRED EMBODIMENTS

Figure 1:
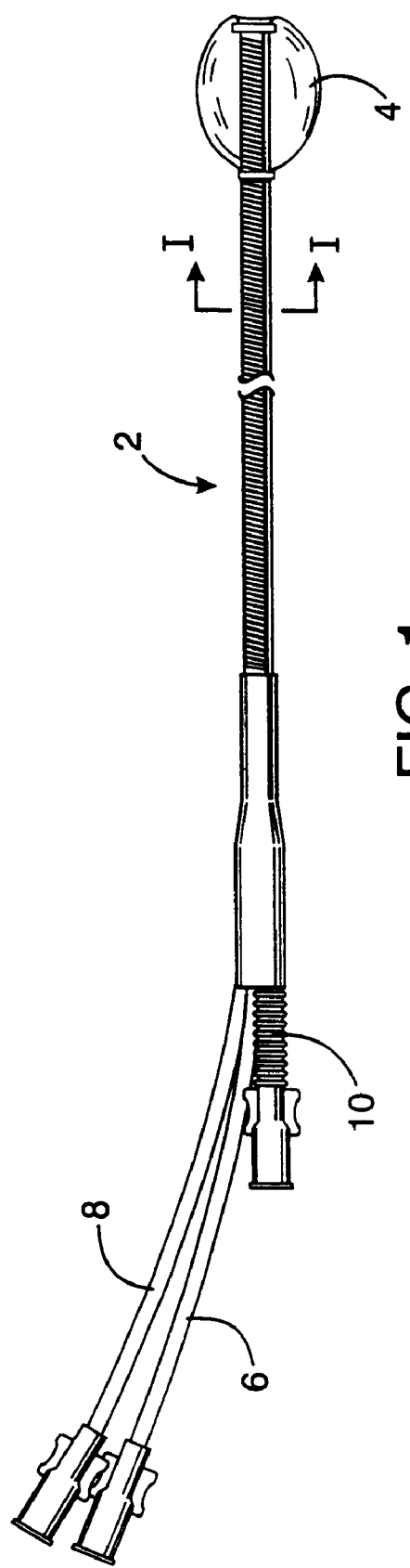
FIG. 1 shows an aortic occlusion device.
Figure 5:
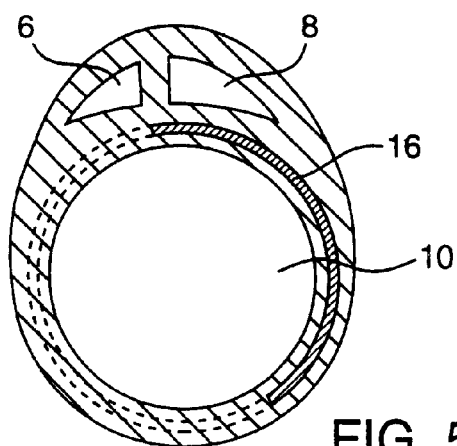
FIG. 5 is a cross-sectional view of FIG. 1 along line I—I.

Referring to FIGS. 1 and 5, an aortic occlusion device 2 is shown. The aortic occlusion device 2 has an occluding member 4 configured to occlude a patient's ascending aorta. The occluding member 4 is preferably a balloon but may also be a mechanically actuated member. The aortic occlusion device 2 has an inflation lumen 6 for inflating the occluding member 4, a pressure lumen 8 for measuring pressure in the ascending aorta, and a lumen 10 for delivering cardioplegic fluid and/or venting the ascending aorta. The aortic occlusion device 2 is preferably manufactured and used in the manner described in U.S. patent application Ser. No. 08/782,113 but may also be manufactured in any other manner such as an extrusion.

The aortic occlusion device 2 is preferably substantially straight in an unbiased position, however, the aortic occlusion device 2 may also have a shaped end. For example, the aortic occlusion catheter 2 can have an L-shaped end which facilitates positioning the occluding member 4 in the ascending aorta depending upon the surgical approach. The aortic occlusion device 2 is preferably flexible so that it can be bent as necessary without kinking.

Figure 2:
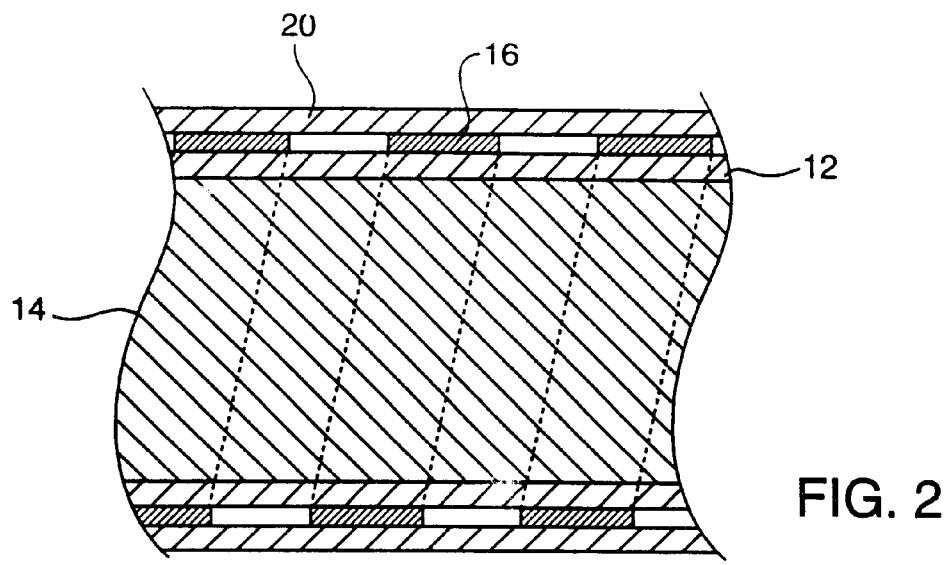
FIG. 2 is a cross-sectional view of a first step in forming the aortic occlusion catheter of FIG. 1.
Figure 3:
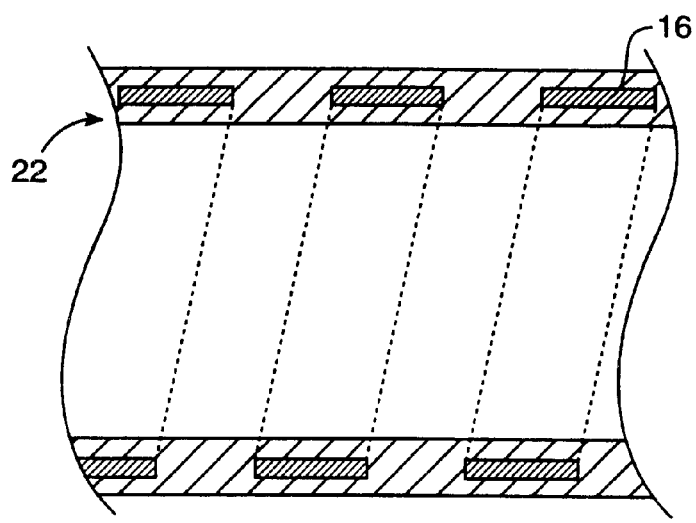
FIG. 3 is a cross-sectional view of the structure of FIG. 2 after heating.

Referring to FIGS. 2–5, a preferred method of forming the aortic occlusion device 2 is shown. FIG. 2 shows a longitudinal cross-section of a tube 12, preferably a urethane tube, mounted on a teflon-coated mandrel 14 with the elongate element 16 wound helically around the tube 12. The elongate element 16 is preferably a wire ribbon having a thickness of 0.003 inch and a width of 0.012 inch. The elongate element 16 is preferably wrapped around the tube 12 with a spacing of 0.010 inch. Another tube 20 is positioned over the elongate member 16 and a shrink tube (not shown) is positioned over the tube 20. The entire structure is then heated to fuse the tubes together to form a reinforced tube 22 which is shown in longitudinal crosssection in FIG. 3. The resulting reinforced tube 22 preferably has an inner diameter of about 0.100 inch and a wall thickness of about 0.010 inch.

Figure 4:
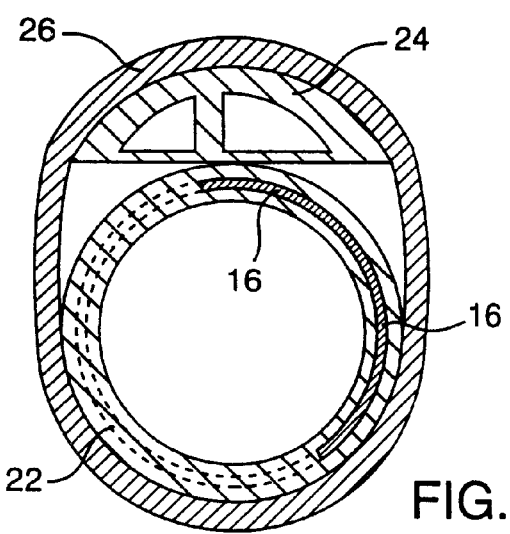
FIG. 4 is a cross-sectional view of a further step in forming the aortic occlusion catheter of FIG. 1.

Referring to FIG. 4, a two-lumen member 24 is positioned against the reinforced tube 22 and a shrink tube 26 is positioned around the member 24 and reinforced tube 22. The two-lumen member 24 has the inflation lumen 6, which is used for inflating the occluding member 4, and the pressure lumen 8, which is used for pressure monitoring in the ascending aorta. The two-lumen member 24 is preferably an extrusion having a D-shaped outer surface in cross-section. The member 24 and tube 22 are then heated and the shrink tube 26 is removed to obtain the egg-shaped cross-sectional shape shown in FIG. 5. The cross-sectional shape is preferably about 0.145 inch tall and 0.125 inch wide. The inflation lumen 6 is then pierced to provide an inflation path to the occluding member 4 and the occluding member 4 is then mounted to the shaft.

Referring to FIGS. 6 and 7, a cannula 28 is shown which is used to return oxygenated blood to the patient when the patient's heart is arrested. The aortic occlusion device 2 is introduced into the patient through the cannula 28 as will be described below. The cannula 28 has a y-arm connector 30 with first and second arms 32, 34 with each coupled to a lumen 35. The second arm 34 has a hemostasis valve 36 which may be any hemostasis valve and is preferably a Thouy-Borst valve. The cannula 28 has a reinforced body 38 which is preferably formed in the manner described in U.S. Pat. No. 5,863,366, which is hereby incorporated by reference, however, any other method may be used including extrusion. The distal end 40 of the cannula 28 is beveled and has an open end 42 and two side ports 44 for infusing oxygenated blood into the patient. A radiopaque markers 45 are provided at the distal end for visualization as discussed below.

Figure 9:
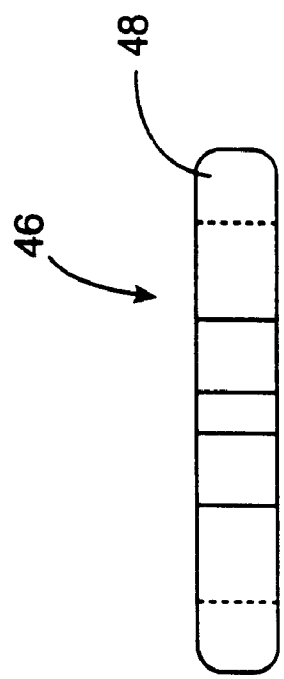
FIG. 9 is a side view of the ring.
Figure 8:
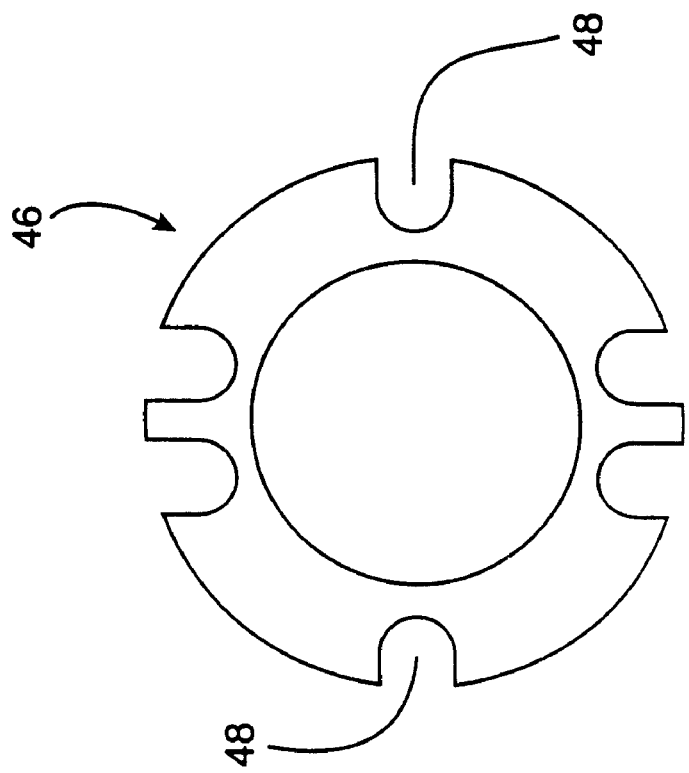
FIG. 8 is a plan view of a ring.

Referring to FIGS. 6–9, a ring 46 is attached to the distal end 40 of the cannula 28. The ring 46 limits insertion of the cannula 28 into the vessel, stabilizes the cannula 28, and receives purse-string sutures which provide hemostasis around the cannula 28 when the cannula 28 is positioned in a vessel. Referring to FIGS. 8 and 9, the ring 46 has slots 48 which may receive purse-string sutures as will be described below.

Figure 10:
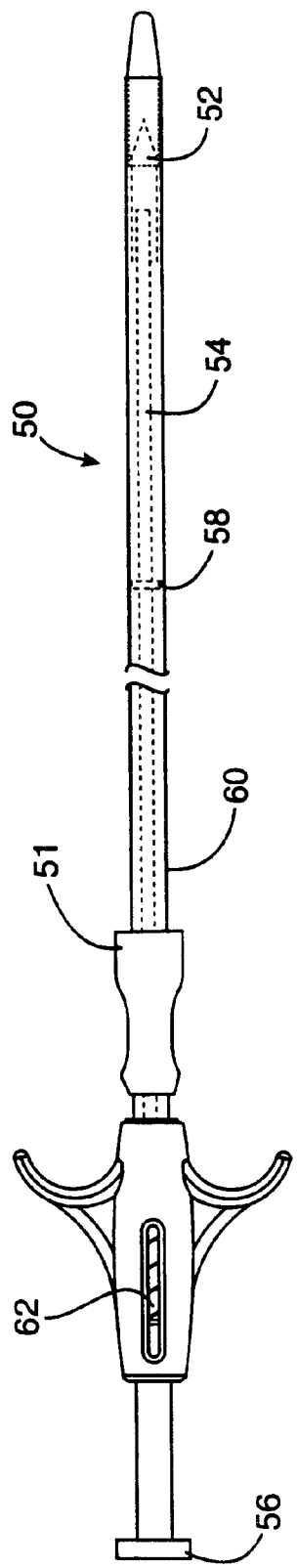
FIG. 10 shows an introducer with an incising element in a retracted position.
Figure 11:
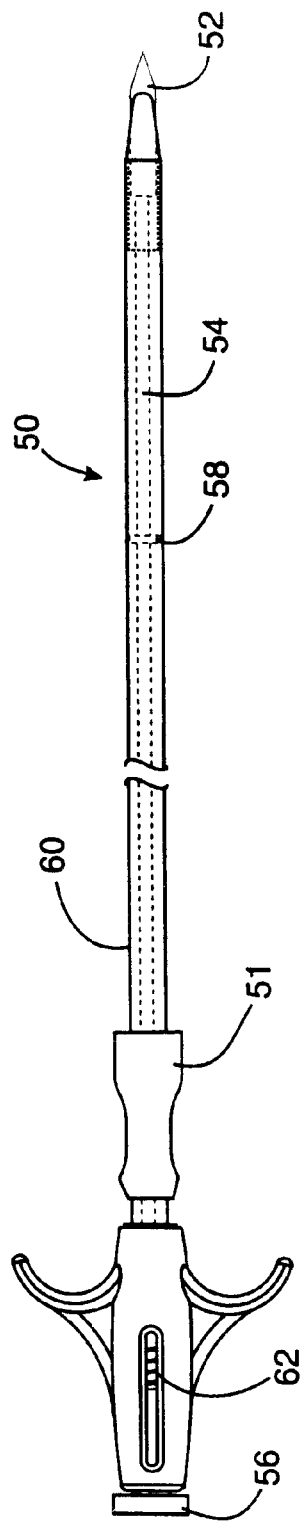
FIG. 11 shows the introducer with the incising element in an exposed position.

Referring to FIGS. 10 and 11, an introducer 50 is positioned in the cannula 28 to introduce the cannula 28 into a vessel. The introducer 50 has a connector hub 51 which is received by the hemostasis valve 36 on the second arm 32 of the cannula 28 to seal the space between the introducer 50 and cannula 28. The introducer 50 has an incising element 52 for incising the vessel into which the cannula 28 is introduced. The incising element 52 is attached to a shaft 54 which is coupled to a trigger 56 for moving the incising element 52 from the retracted position of FIG. 10 to the exposed position of FIG. 11. An o-ring seals 58 the space between an outer housing 60 and the shaft 54. The incising element 52 is biased toward the retracted position by a spring 62 so that the incising element 52 is only exposed when the trigger 56 is actuated. When introducing the cannula 28 into the vessel, the trigger 56 is actuated to move the incising element 52 to the exposed position, the vessel is incised with the incising element 52 and the cannula 28 is inserted through the incision. As will be described below, one or more purse-string sutures are then used to form a hemostatic seal around the cannula 28. The incising element 52 may be omitted if a separate incising device is used.

Figure 12:
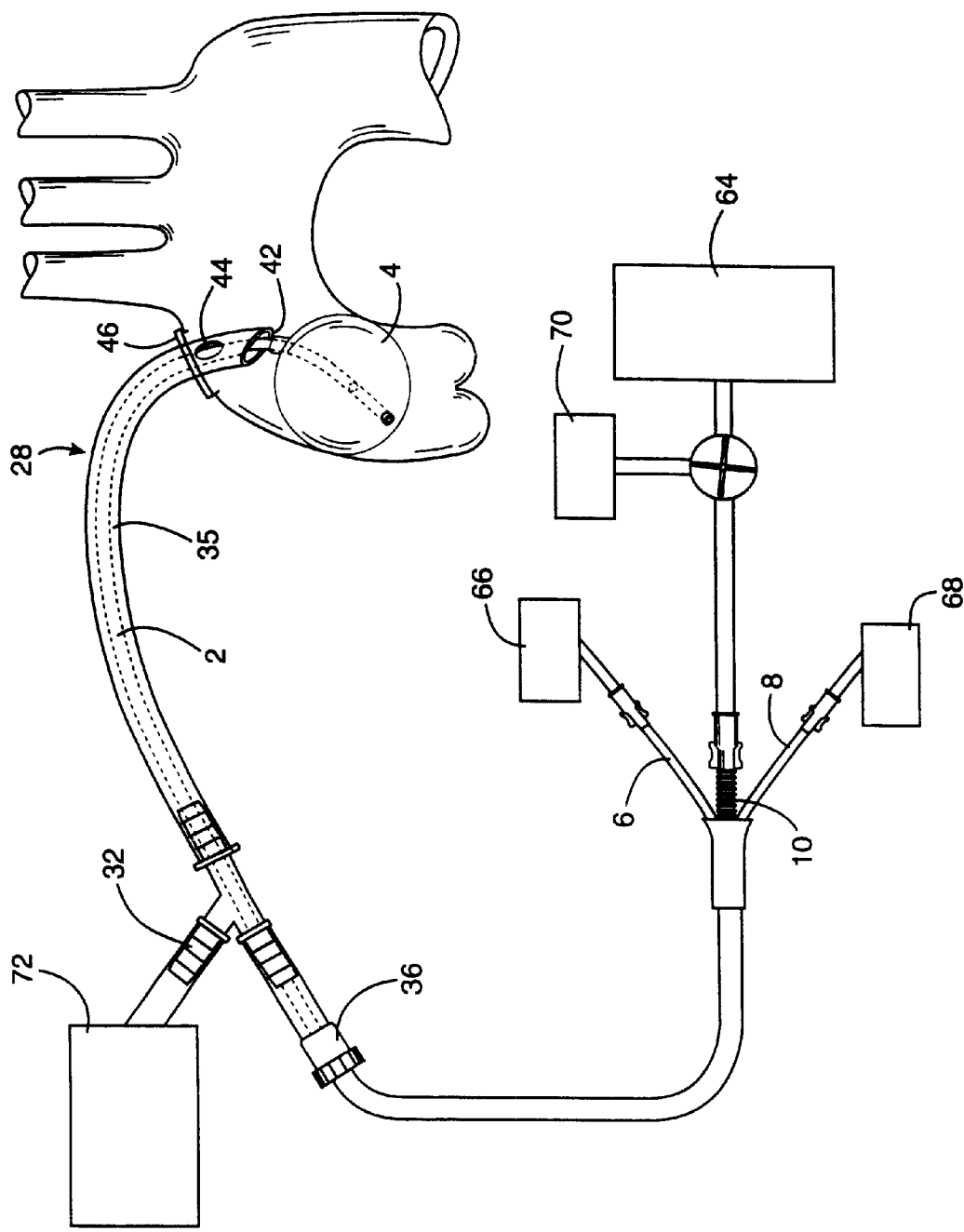
FIG. 12 shows the aortic occlusion device and cannula passing through a penetration in the ascending aorta.

Referring to FIG. 12, the cannula 28 is positioned in a patient's ascending aorta with the aortic occlusion device 2 passing through the hemostasis valve 36 . Placement of the cannula 28 and aortic occlusion device 2 into the position of FIG. 12 is described below. Referring to FIGS. 5 and 12, the lumen 10 is coupled to a source of cardioplegic fluid 64, the inflation lumen 6 is coupled to a source of inflation fluid 66, and the pressure lumen 8 is coupled to the pressure monitor 68 for measuring pressure in the ascending aorta. The lumen 10 is also coupled to a vacuum source 70 for venting the ascending aorta.

The first arm 32 of the cannula 28 is coupled to a source of oxygenated blood 72 so that blood is delivered through the lumen 35 of the cannula 28 with the blood passing through the annular area between the cannula 28 and the aortic occlusion device 2. The oxygenated blood passing through the open end 42 of the cannula 28 is directed at the occluding member 4 so that the oxygenated blood is not directed at the wall of the aorta. An advantage of directing the oxygenated blood at the occluding member 4 is that the fluid is dispersed radially outward by the occluding member 4 before coming into contact with the wall of the aorta. By directing the blood at the occluding member 4, rather than at the wall of the aorta, the likelihood of releasing emboli from the wall of the aorta may be reduced. Oxygenated blood is also directed through the side ports 44 so that oxygenated blood is delivered to the patient even if the occluding member 4 blocks the open end 42 of the cannula 28.

Figure 13:
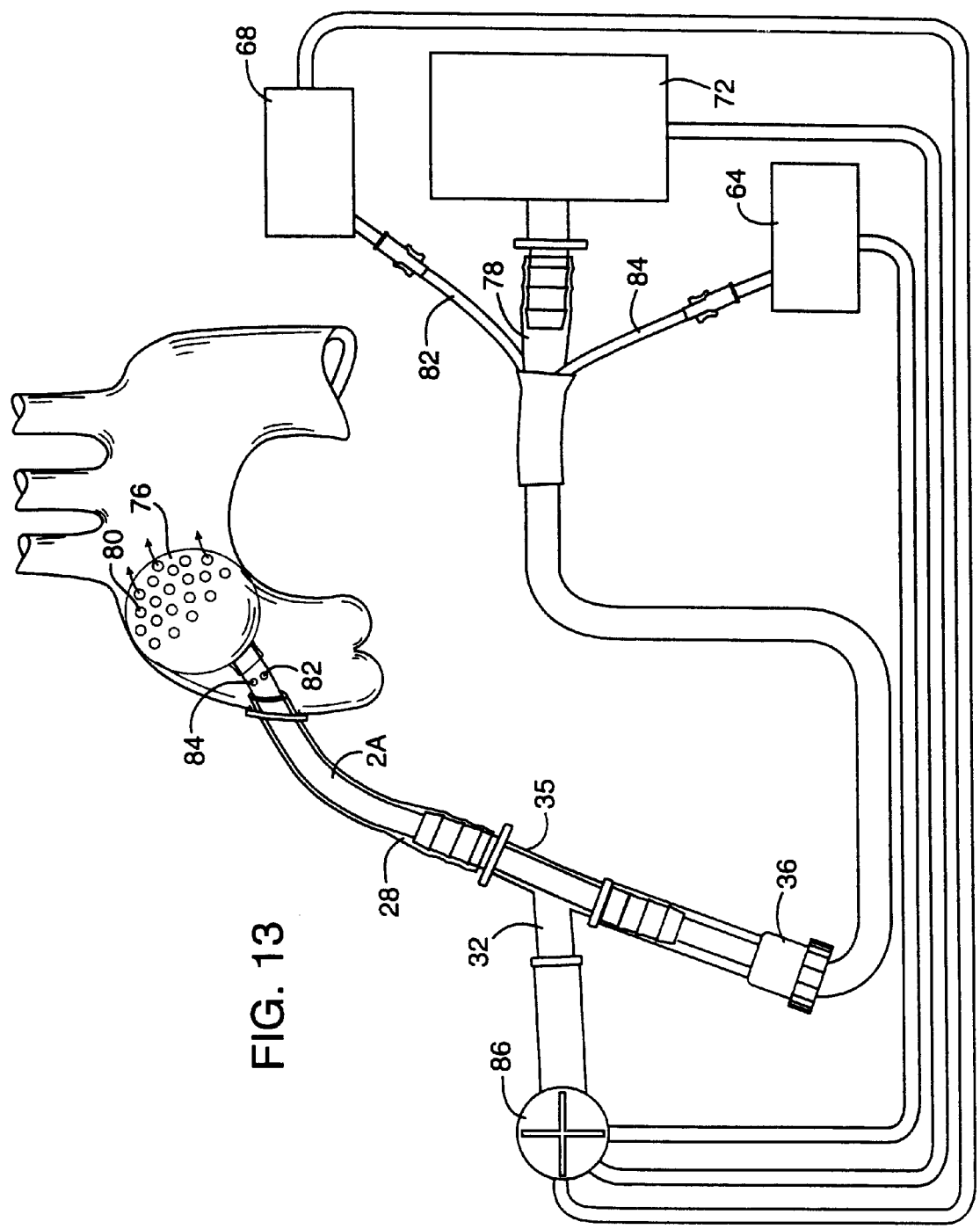
FIG. 13 shows another aortic occlusion device passing through the cannula and into the patient's ascending aorta.

Referring to FIG. 13, another aortic occlusion device 2A is shown having a balloon 76 which is inflated with the oxygenated blood delivered to the patient. The aortic occlusion device 2A has a blood flow lumen 78 which is fluidly coupled to the interior of the balloon 76 for inflating the balloon 76. Oxygenated blood is then delivered to the patient through an opening 80, preferably a number of openings, in the balloon 76. An advantage of the aortic occlusion device 2A is that a separate inflation lumen is not required since occlusion is accomplished by simply delivering oxygenated blood through the aortic occlusion device 2A. The aortic occlusion device 2A may also include a pressure lumen 82 for measuring pressure in the ascending aorta and a lumen 84 for delivering cardioplege and venting the ascending aorta. The aortic occlusion device 2A is preferably formed in the manner described above except that the lumen 78 is sized large enough to provide sufficient flow of oxygenated blood at an acceptable pressure. Acceptable blood flow rates and pressures are disclosed in the above-mentioned patents and patent applications which have been incorporated by reference. Although it is preferred to manufacture the device in the manner described above, the aortic occlusion device 2A may also simply be an extrusion or laminated structure. The balloon 76 is preferably made of silicone having a thickness of between 0.005 and 0.009 inch.

The aortic occlusion catheter 2A passes through the cannula 28 so that oxygenated blood can be delivered to the patient when the aortic occlusion device 2A is removed. The cannula 28 is preferably the cannula 28 described above with the first arm 32 coupled to the source of oxygenated blood 72, pressure monitor 68, and source of cardioplegic fluid via valve 86. Thus, cardioplegic fluid and oxygenated blood can be directed through the lumen 35 in the cannula 28 if the lumen 84 is not provided in the aortic occlusion catheter 2A. The cannula 28 has the hemostasis valve 36 to seal the space between the cannula 28 and aortic occlusion device 2A.

Figure 14:
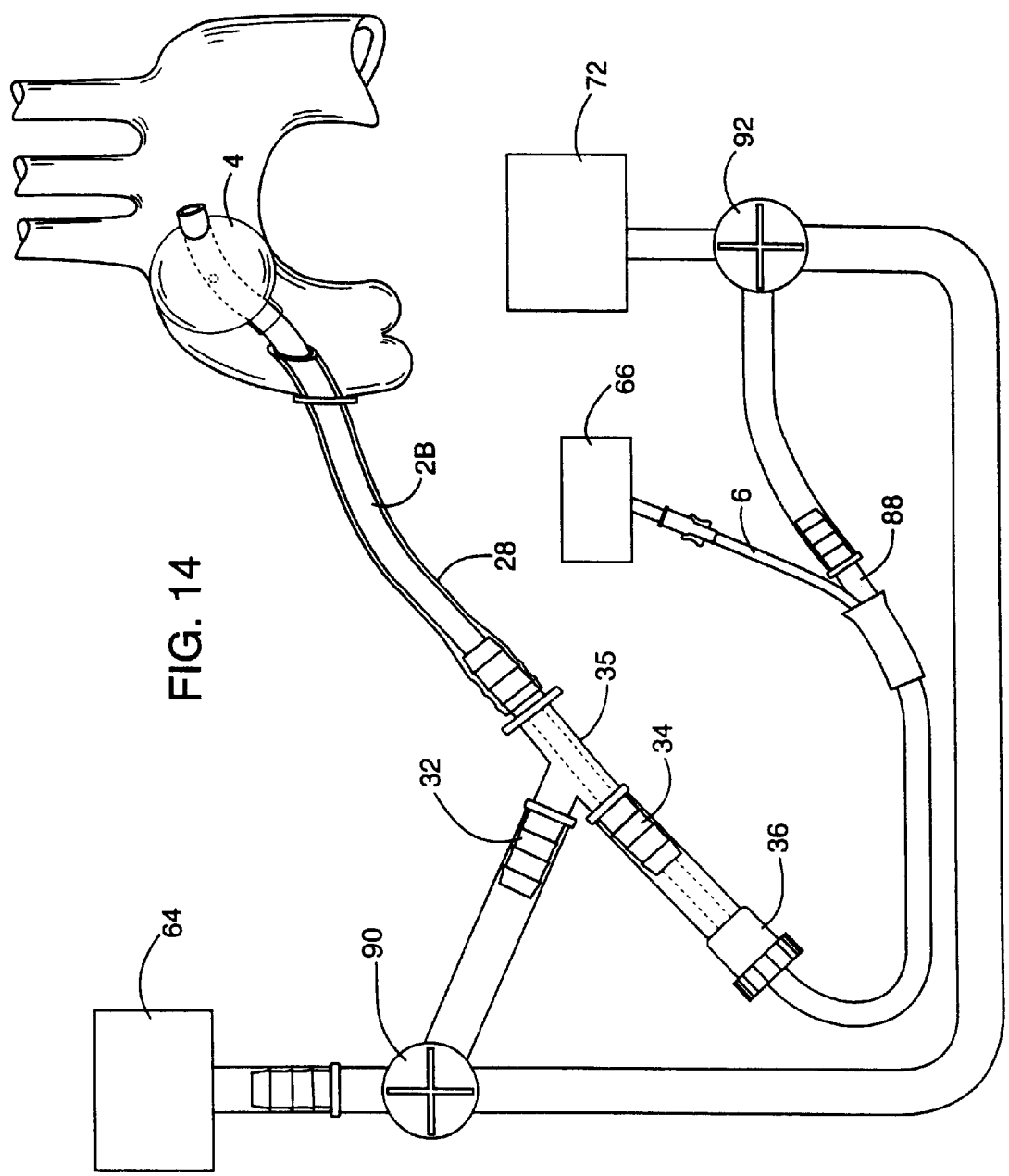
FIG. 14 shows yet another aortic occlusion device.

Referring to FIG. 14, yet another aortic occlusion device 2B is shown. The aortic occlusion device 2B has the occluding member 4 and the inflation lumen 6 coupled to the source of inflation fluid 66 for inflating the occluding member 4. The aortic occlusion device 2B also has a lumen 88 for delivering oxygenated blood to the patient from the source of oxygenated blood 72. The shaft is preferably reinforced with a wire in the manner described above except that the lumen 88 is sized large enough to provide adequate blood flow to the patient at an acceptable pressure as discussed above. The cannula 28 is preferably the same as the cannula 28 described above and the aortic occlusion device 2B is introduced through the cannula 28 in the manner described below. The first arm 34 of the cannula 28 has the hemostasis valve 36 for receiving the aortic occlusion device 2B. The second arm 32 is coupled to a valve 90 which determines whether cardioplegic fluid or oxygenated blood is delivered through the lumen 35 in the cannula 28. Valve 92 determines whether oxygenated blood is delivered through the lumen 35 in the cannula 28 or the lumen 88 in the aortic occlusion device 2B. An advantage of the aortic occlusion device 2B and cannula 28 is that bypass support can be provided before inflating the occluding member 4 and can also be maintained after the aortic occlusion device 2B is removed from the cannula 28.

Figure 15:
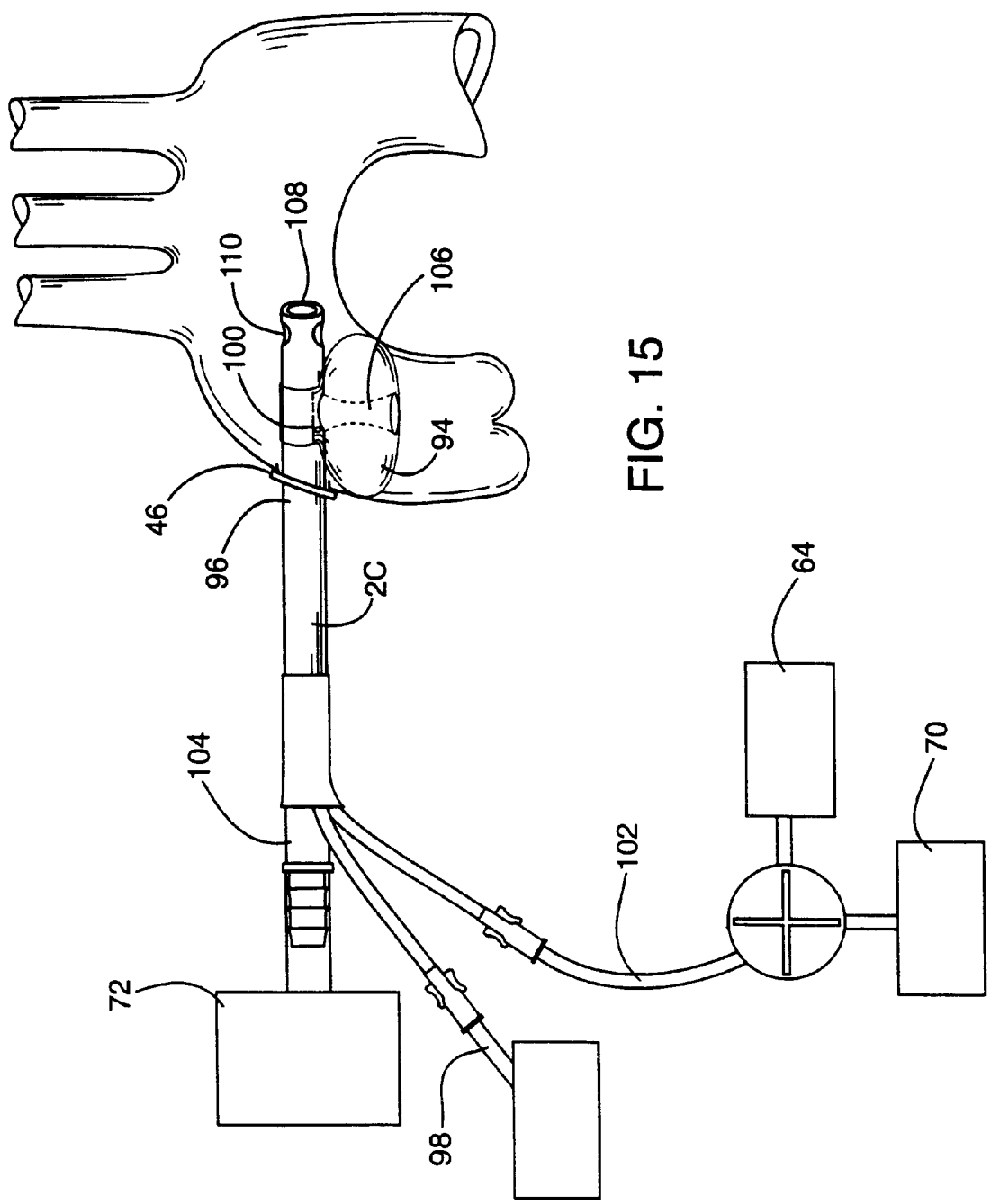
FIG. 15 shows still another aortic occlusion device.

Referring to FIG. 15, another aortic occlusion device 2C is shown. The aortic occlusion device 2C has a balloon 94 mounted to a side of a shaft 96. The aortic occlusion device 2C has an inflation lumen 98 for inflating the balloon 94 through inflation outlet 100 and a lumen 102 for delivering cardioplegic fluid from the source of cardioplegic fluid 64 and venting the ascending aorta using the vacuum source 70. The aortic occlusion device 2C also has a blood flow lumen 104 for delivering oxygenated blood to the patient from the source of oxygenated blood 72. A fluid path 106 passes through the balloon 94 which is in fluid communication with the lumen 102 so that cardioplegic fluid is delivered through the fluid path 106 in the balloon 94. An advantage of the aortic occlusion device 2C is that the cardioplegic fluid can be delivered toward the aortic valve while oxygenated blood is directed in the direction of normal blood flow in the aortic arch. The distal end of the aortic occlusion device has an open end 108 and side ports 110 through which the oxygenated blood is delivered. The aortic occlusion device 2C also includes the ring 46 which is the same as the ring 46 described above. The aortic occlusion device 2C may be manufactured in any manner such as the manner described above or as a simple extrusion or laminated structure.

Figure 16:
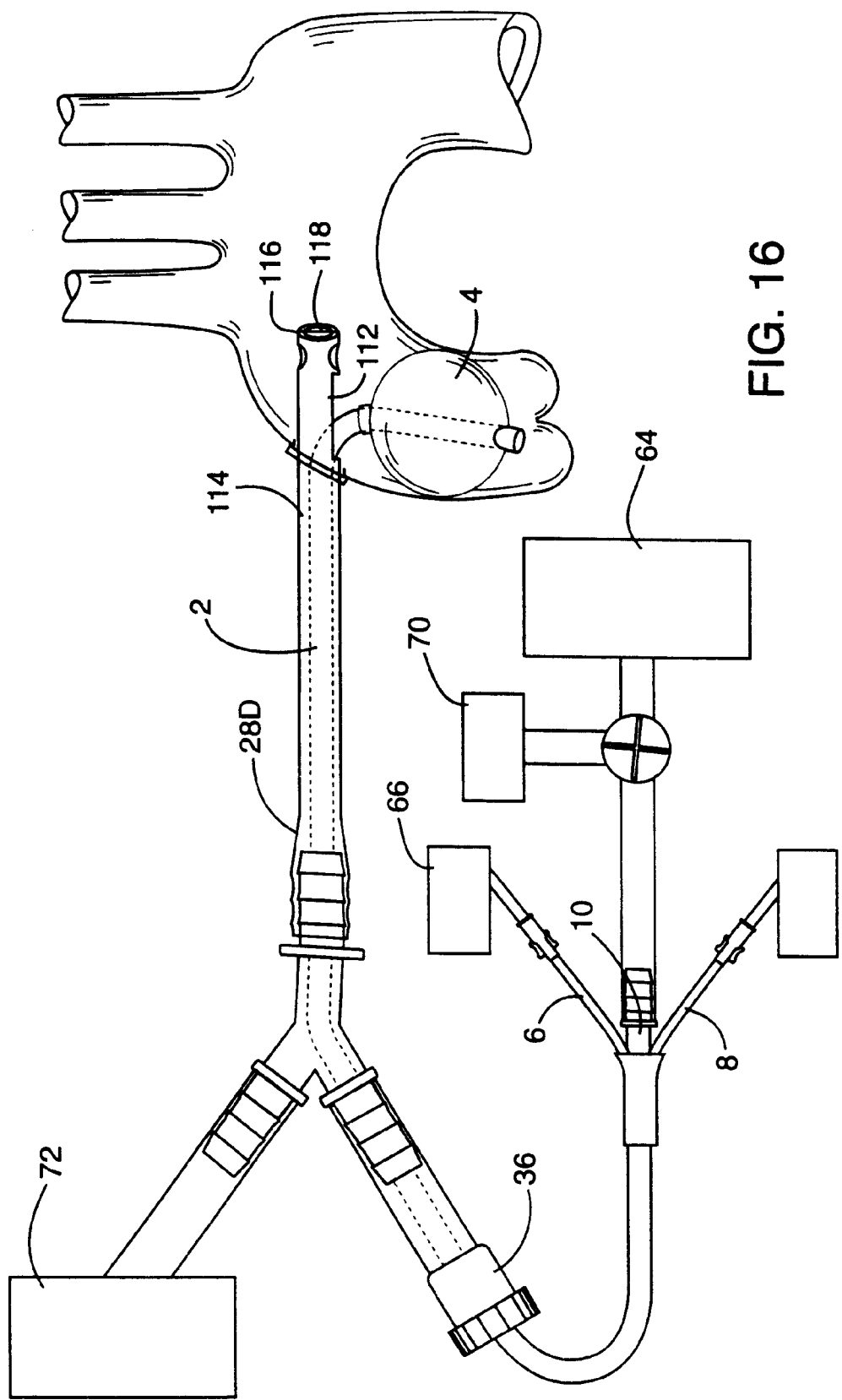
FIG. 16 shows a final aortic occlusion device.

Referring to FIG. 16, the aortic occlusion device 2 is shown passing through a side port 112 of a cannula 28D. The side port 112 facilitates positioning the occluding member 4 in the ascending aorta. The aortic occlusion device 2 is preferably the aortic occlusion device 2 described above. The aortic occlusion device 2 passes through a lumen 114 in the cannula 28D. The lumen 114 is coupled to the source of oxygenated blood 72 so that the oxygenated blood is delivered through the annular area between the aortic occlusion device 2 and the wall of the lumen 114. The lumen 114 has an open end 116 with a cross-member 118 which prevents the aortic occlusion catheter 2 from passing through the open end 116. An advantage of the side port 112 is that the aortic occlusion device 2 is directed into the ascending aorta while blood passing through the lumen 114 is directed in the direction of normal blood flow in the aorta.

Referring to FIGS. 18 and 19, another aortic occlusion device 2E is shown. The aortic occlusion device 2E is similar to the aortic occlusion device 2A of FIG. 13 in that balloon 130 is inflated with oxygenated blood delivered from the source of oxygenated blood 72. Oxygenated blood is delivered to the patient through a lumen 132 and an open end 134 of the aortic occlusion device 2E. As will be described below, the interior of the balloon 130 is fluidly coupled to the lumen 132 through an inflation hole 133 for inflating the balloon 130 when blood is delivered through the lumen 132.

The aortic occlusion device 2E includes a body 136 having the y-arm connector 30 described above. A sleeve 138 is positioned in the lumen 132 to control inflation and deflation of the balloon 130. Blood passing through the lumen 132 passes through the sleeve 138 so that the sleeve 138 does not interfere with delivery of oxygenated blood to the patient. The sleeve 138 is attached to a rod 140 which is manipulated to move the sleeve 138 between the positions of FIGS. 18 and 19. The sleeve 138 has a hole 142 which is alligned with the inflation hole 133 as shown in FIG. 18 to fluidly couple the interior of the balloon 130 with the lumen 132. When the sleeve 138 is advanced to the position of FIG. 19, the hole 142 is not alligned with the inflation lumen 133 and the sleeve 138 covers the inflation hole 133 so that the interior of the balloon 130 is not fluidly coupled to the lumen 132.

The sleeve 138 permits the surgeon to control inflation and deflation of the balloon 130. After introduction of the aortic occlusion device 2E, bypass support is generally initiated before inflating the balloon 130. This can be accomplished by maintaining the sleeve 138 in the position of FIG. 19 so that the balloon 130 is not inflated by the blood delivered through the lumen 132. When it is desired to inflate the balloon 130 and occlude the ascending aorta, the sleeve 138 is moved to the position of FIG. 18 so that the balloon 130 is inflated with blood. The sleeve 138 also permits the surgeon to maintain full occlusion of the ascending aorta even when blood flow is reduced to a level which would not provide sufficient pressure to inflate the balloon to maintain full occlusion of the aorta. In order to maintain occlusion at low flow rates, the sleeve 138 is moved to the position of FIG. 19 before reducing the blood flow rate so that the balloon 130 will remain inflated when the delivery pressure drops. Finally, the sleeve 138 also permits the surgeon to maintain bypass support with a deflated balloon 130 after the surgical procedure is completed. In order to maintain deflation of the balloon while delivering blood, the blood flow rate is reduced to deflate the balloon 130, the sleeve is moved to the position of FIG. 19 to deflate the balloon, and the blood flow rate is then increased. The sleeve 138 prevents the balloon 130 from inflating when the blood flow rate is increased.

The body 136 may be made in any suitable manner and is preferably manufactured similar to the cannula 28 of FIG. 6. A support tube 144 is attached to the body and the balloon 130 is mounted to the support tube. A soft tip 145 is attached to the distal end of the support tube 144 to provide an atraumatic distal end to prevent injury during introduction of the device 2E. The sleeve 138 may be made of any suitable material and is preferably a urethane tube. The rod 140 may also be made of any suitable material and is preferably urethane coated polyamide. Although it is preferred to provide the sleeve 138 between the interior of the balloon 130 and the lumen 132 any other device may be used such as a valve, balloon or plug.

Figure 17:
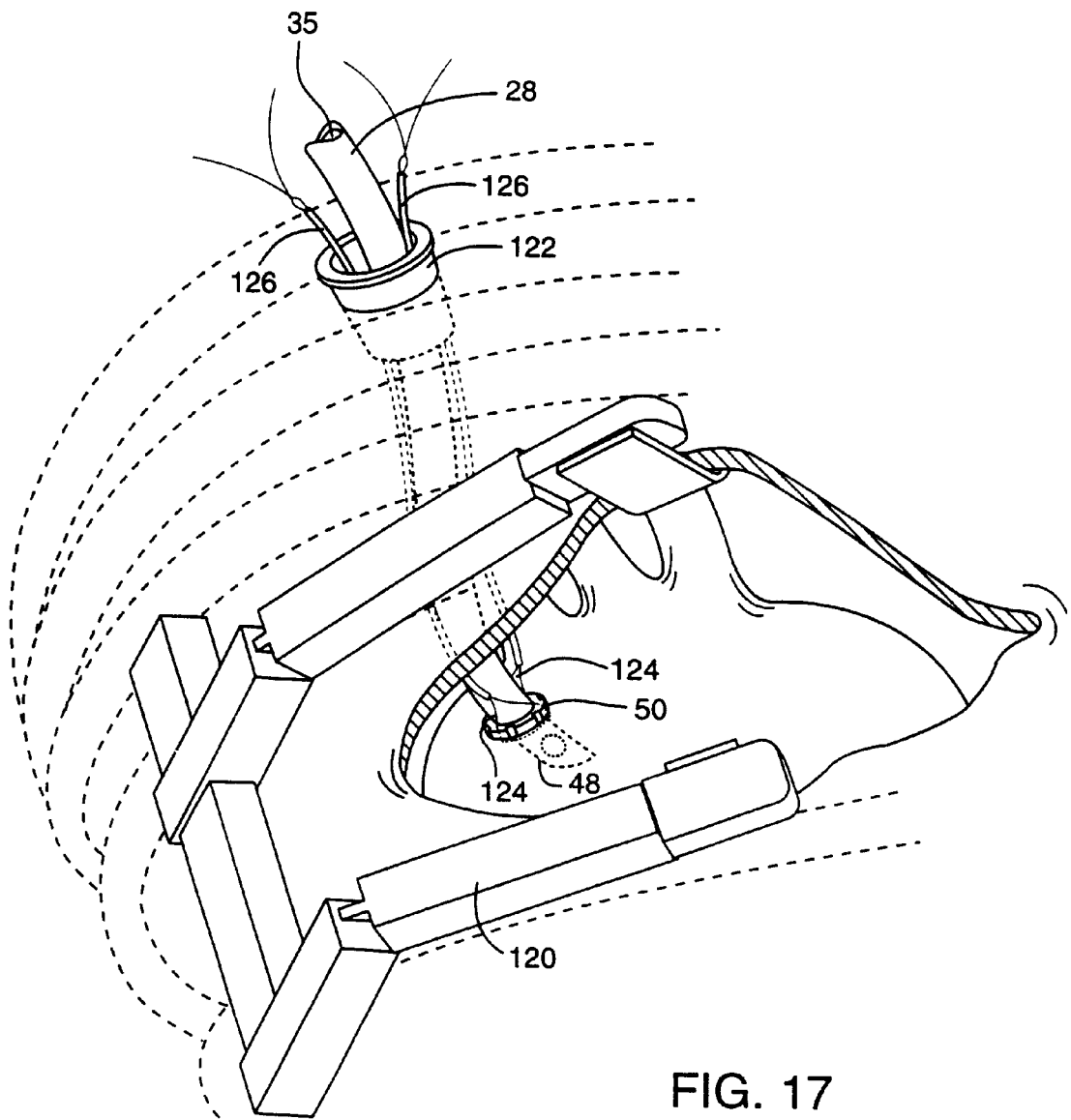
FIG. 17 illustrates a preferred method of introducing the aortic occlusion device.

Use of the cannula and aortic occlusion device 2 is now described in connection with FIGS. 12 and 17. The description below is applicable to all cannulae 28, 28D and aortic occlusion devices 2, 2A, 2B, 2C described herein. Although the method described below is for direct insertion of the cannula 28 and aortic occlusion device 2 into the aortic arch, the cannula 28 and aortic occlusion device 2 may also be introduced through a peripheral artery such as the femoral, subclavian or axillary arteries as described in U.S. Pat. No. 5,484,803.

Before introduction of the cannula, a rib retractor 120 or other device is used to form an opening in an intercostal space such as the $4^{th}$ intercostal space. The opening through the intercostal space is used for access to perform a surgical procedure such as a valve repair or replacement. The opening also provides direct access to the ascending aorta for control of the ascending aorta and to place pursestring sutures in the aorta.

An incision is also created in the $1^{st}$ or $2^{nd}$ intercostal space in which an 11.5 mm trocar 122 is positioned. The cannula 28 is then introduced through the trocar 122 and advanced to the surface of the aorta with the introducer 50 (see FIGS. 10 and 11) positioned in the lumen 35 of the cannula 28 to determine the appropriate orientation of the cannula 28. The distal end of the introducer 50 is then moved into contact with the aorta about 1–2 cm below the origin of the in nominate artery to identify the appropriate location for purse-string sutures 124. The surgeon then places two purse-string sutures 124 around the site. The ends of the purse-string sutures 124 are passed through tubes 126 which are used to tension the purse-string sutures 124. The purse-string sutures 124 are then passed through the slots 48 in the ring 46.

The cannula 28 is then advanced into contact with the aorta at the site now surrounded by the purse-string sutures 124. The surgeon then incises the aorta with the incising element 52 of the introducer 50 or with a separate incising instrument. The cannula 28 is then immediately advanced through the incision until the ring 46 engages the aorta. The radiopaque marker 45 may be viewed under fluoroscopy and the cannula 28 manipulated until the beveled tip is directed toward the aortic valve. Alternatively, the tip orientation may be determined by TEE. The purse-string 124 sutures are then tensioned to seal around the cannula 28. The aortic occlusion device 2 is then passed through the hemostasis valve 36 and advanced until the occluding member 4 is positioned in the ascending aorta. Delivery of oxygenated blood, occlusion of the ascending aorta and delivery of cardioplegic fluid is then performed in the manner described in U.S. Pat. No. 5,484,803.

Referring now to FIGS. 20–24, a cannula 28F is shown wherein the same or similar reference numbers refer to the same or similar structure. The cannula 28F may be used with any of the catheters and cannulae described herein and, thus, the features of the cannula 28F may be included in any of the cannulae or catheters described herein without departing from the invention. For example, the cannula 28F may receive the aortic occlusion catheter 2 (FIG. 24) or have the aortic occlusion member 4 (see FIG. 25). The cannula 28F may also be used to simply deliver blood in conventional open-chest surgery where an external cross-clamp is used to occlude the ascending aorta.

The cannula 28F is similar to the cannula 28 described above except that the cannula 28F has a curved or angled distal portion 130 when in the natural, unbiased shape of FIGS. 20 and 21. An advantage of the curved or angled distal portion 130 is that fluids, such as blood, may be infused or withdrawn from a passageway with the cannula 28F directed with or against natural flow. Another advantage of the curved or angled distal end 130 is that the cannula 28F is centered in the vessel so that fluid infused through the cannula 28F is not directed at a wall. The cannula also helps to center the catheter 2 extending from the distal end of the cannula 28F. Centering the catheter 2 ensures that the distal tip of the catheter 2 is centered in the vessel rather than directed at a vessel wall to facilitate fluid infusion or venting through the catheter 2 as described above. The distal portion 130 also helps anchor the catheter 2 and occluding member 4 in the vessel to resist migration of the catheter 2 and distortion of the occluding member 4.

Figure 22:
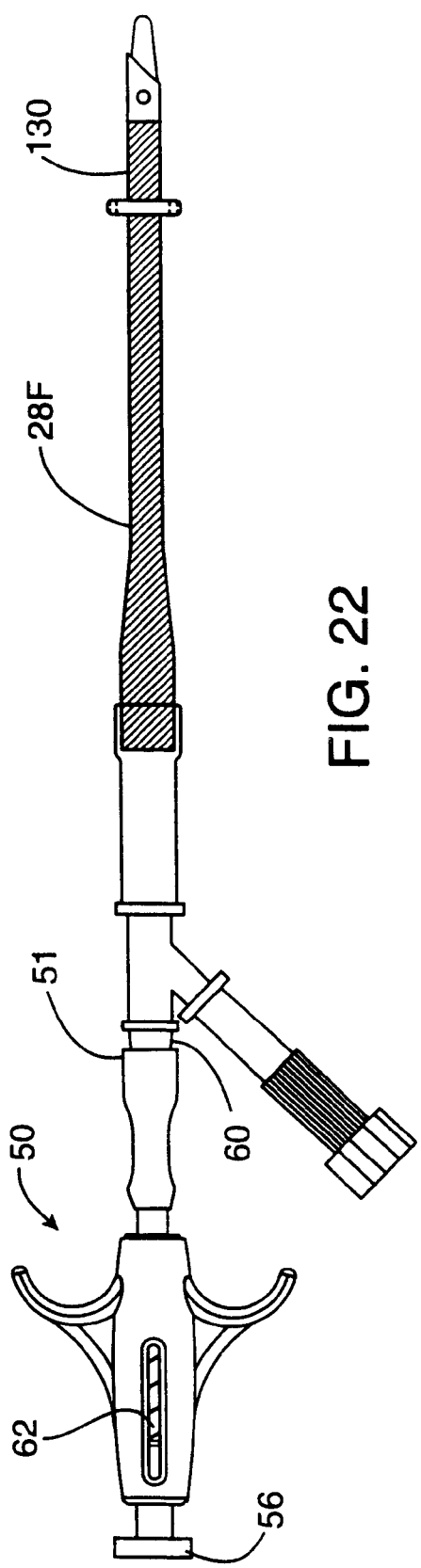
FIG. 22 shows the cannula of FIG. 20 with the introducer straightening the distal portion.

Referring to FIG. 22, the introducer 50 straightens the distal portion 130 of the cannula 28F for introduction of the cannula 28F into a vessel. The straightened configuration facilitates introduction since the cannula 28F is advanced into the vessel with simple linear motion from the proximal end of the device. Although it is preferred to use the introducer 50 described above, any other suitable introducer may be used including an introducer without an incising element. The cannula 28F preferably includes the y-arm connector 30 having the first and second arms 32, 34 each coupled to the lumen 35. The y-arm connector 30 has the hemostasis valve 36 for receiving a catheter such as any of the aortic occlusion catheters 2, 2A, 2B described herein. The cannula 28F is preferably manufactured in substantially the same manner as cannula 28 described above, however, cannula 28F may be also made in any other suitable manner such as extrusion molding.

Figure 23:
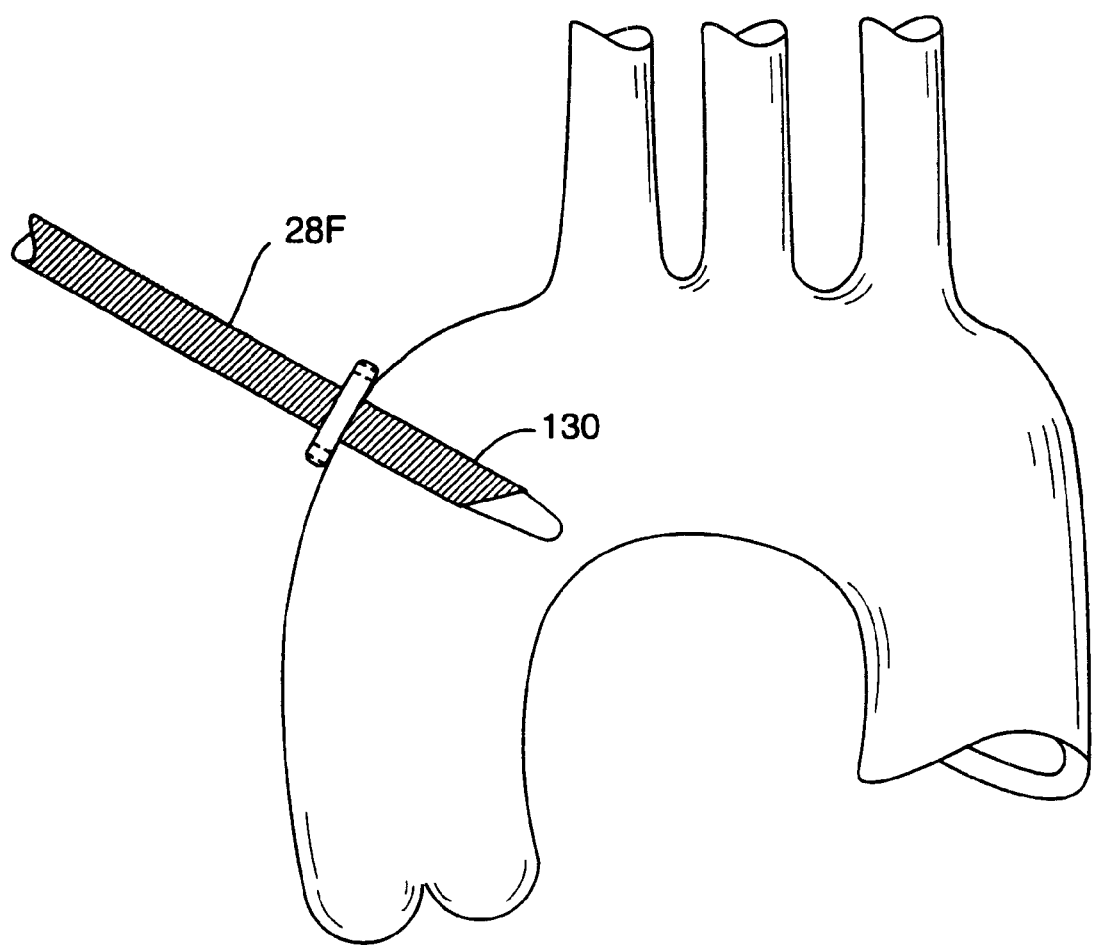
FIG. 23 illustrates introduction of the cannula.
Figure 24:
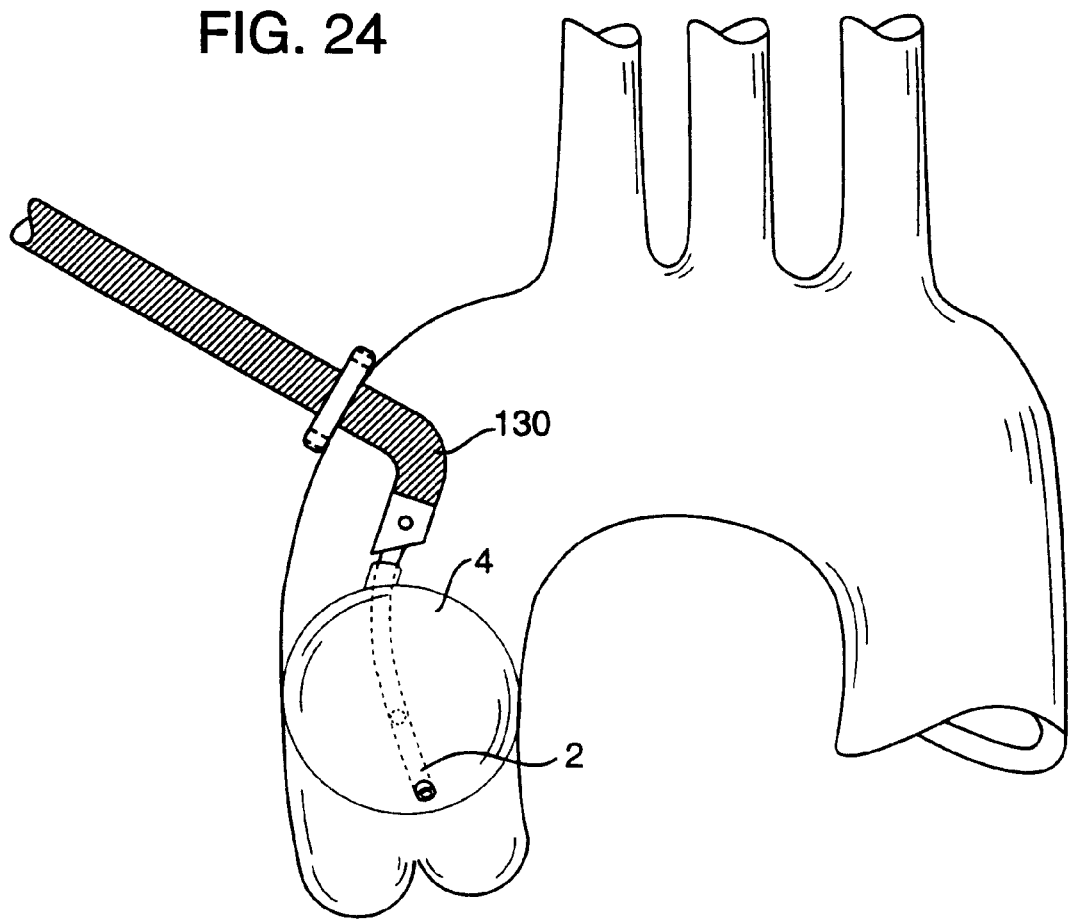
FIG. 24 shows the aortic occlusion device passed through the cannula.
Figure 25:
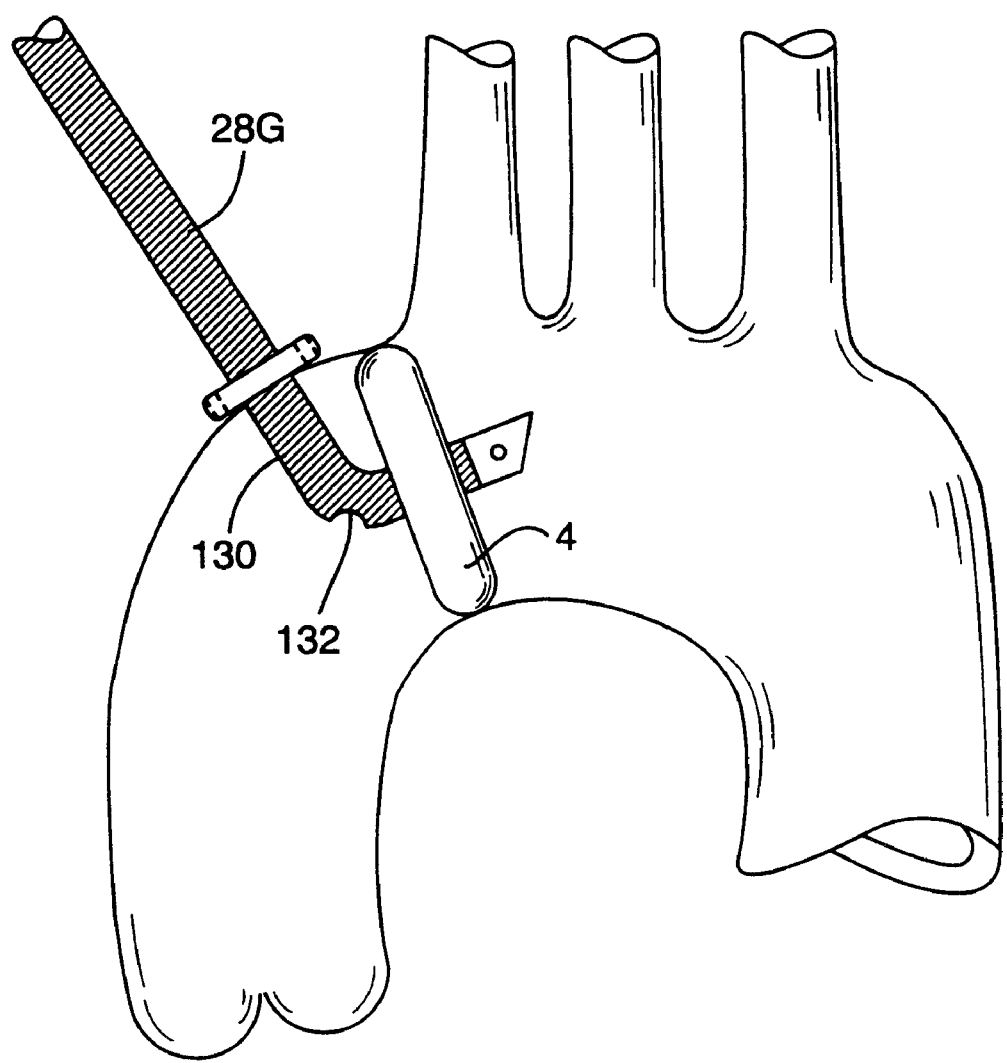
FIG. 25 shows the cannula of FIG. 20 including an occluding member.

Use of the cannula 28F is now described in connection with FIGS. 23 and 24. As mentioned above, all features of the cannula 28F may be included in any of the cannulae and catheters described herein and description of the method is applicable to all of the cannulae and catheters. Purse-string sutures (not shown) are sewn in the aorta to provide hemostasis around the cannula. The cannula 28F is moved toward the aorta and the incising element 52 (see FIG. 11) is extended to incise the aorta. The cannula 28F is then advanced into the aorta, the incising element 52 is retracted and the purse-string sutures are tensioned. The introducer 50 is then removed which permits the distal portion 130 of the cannula 28F to curve or angle in the manner shown in FIG. 24. Catheters, such as the aortic occlusion device 2, can then be advanced into the aorta as described above for occlusion of the aorta, delivery of cardioplegic fluid and return of oxygenated blood. Alternatively, the cannula 28F may be oriented downstream to simply deliver blood from a bypass system. Referring to FIG. 25, another cannula 28G is shown which includes the occluding member 4 and lumen 132 for venting and delivery of cardioplegic fluid.

Figure 26:
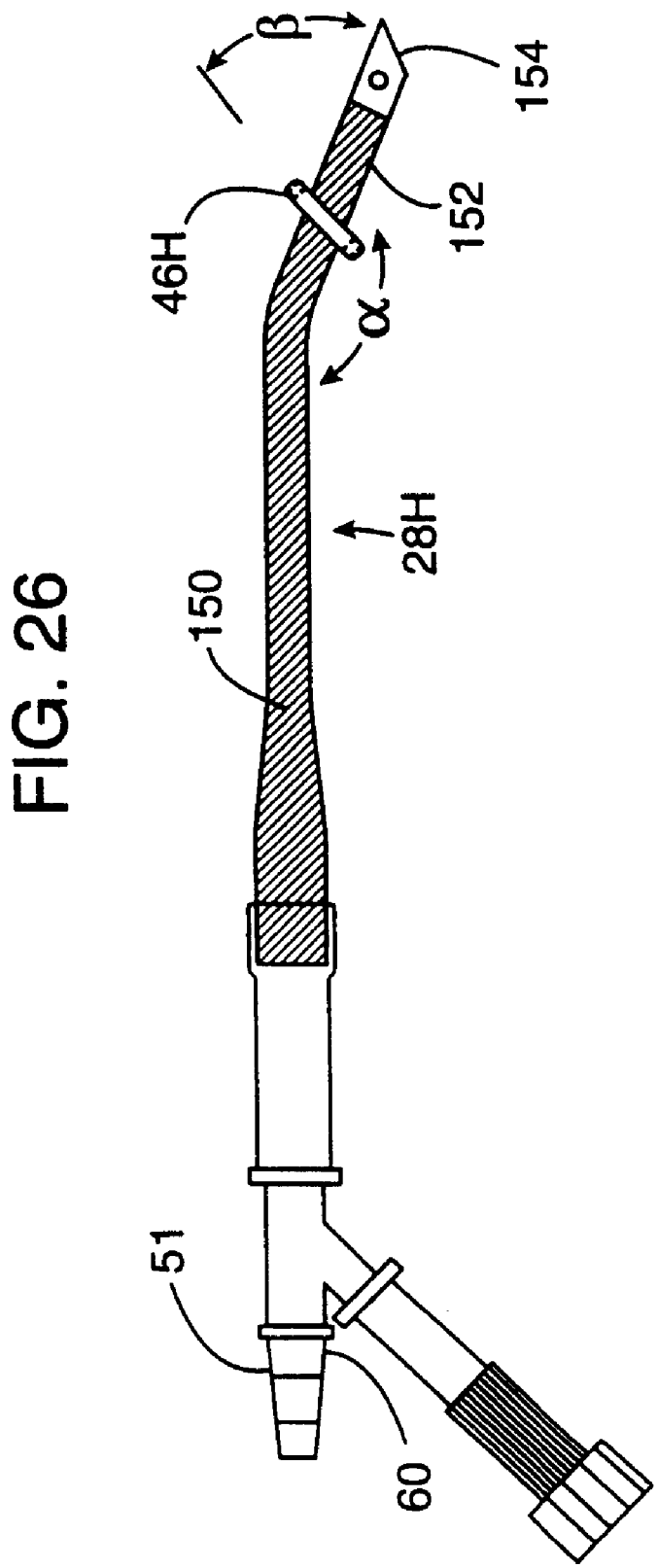
FIG. 26 shows another cannula having a angled shaft and an angled stabilizing ring.
Figure 27:
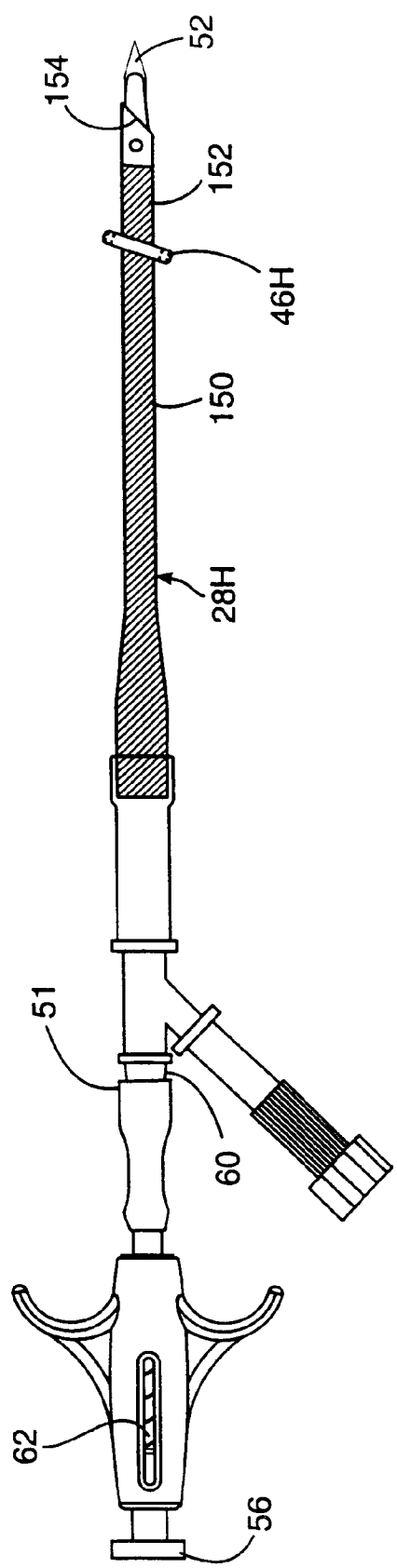
FIG. 27 shows the cannula of FIG. 26 with the introducer straightening the shaft.

Referring to FIGS. 26 and 27, another cannula 28H is shown wherein the same or similar reference numbers refer to the same or similar structure. The cannula 28H has an angled shape to move the shaft out of the surgical field and away from the surgeon so that the cannula 28H does not interfere with the procedure. The angled shape is particularly useful when introducing the cannula 28H through small incisions between the ribs such as an incision in the first or second intercostal space. The cannula 28H may, of course, be introduced through a median sternotomy, thoracotomy or other surgical incision without departing from the scope of the invention.

The cannula 28H has a first section 150 extending from the y-arm connector 30 to a second section 152 which is angled with respect to the first section 150. The second section 152 extends for 2–6 cm and more preferably 3–4 cm from a distal end 154. The first section 150 forms an angle α with the second section 152 of about 110 to 140 degrees and more preferably about 125 degrees. The stabilizing ring 46H is mounted to the first section 150 and preferably forms an angle β of about 45 to 85 degrees and more preferably about 60–75 degrees with the first section 150. The ring 46H is preferably attached to the second section 152 about 3–4 cm from the distal end 154. The cannula 28H may be used as a substitute for any of the other cannulae 28H described herein and, thus, the cannula 28H may receive catheters 2, 2A, 2B, have the occluding member 4 or may be used to simply return blood to the patient from a bypass system. The cannula 28H may be manufactured in any suitable manner and is preferably manufactured in a substantially similar manner to the cannula 28 described above.

Figure 28:
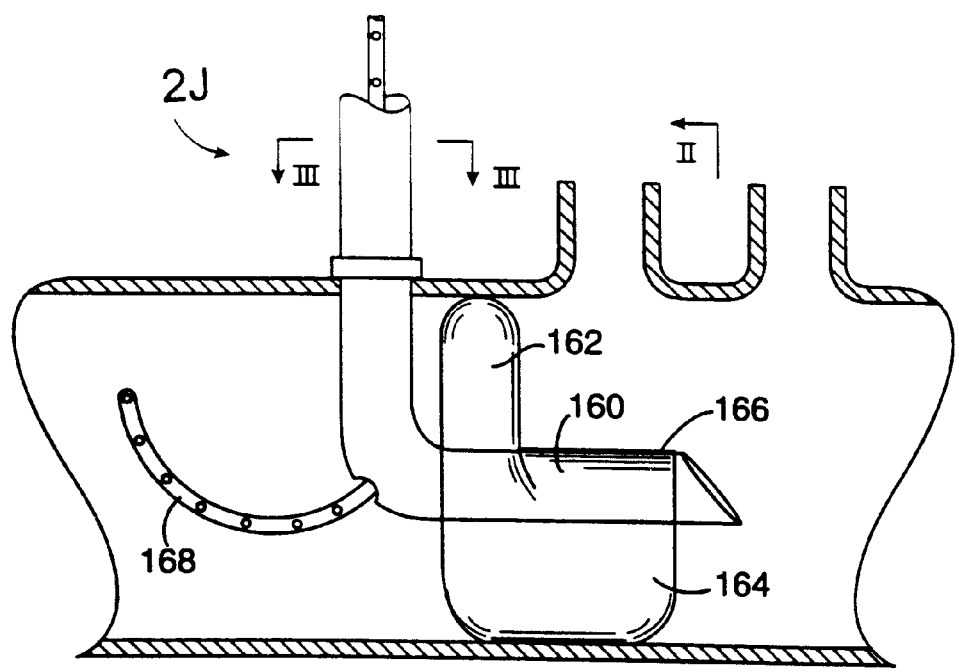
FIG. 28 shows a balloon having a first, smaller section stabilized by a second, larger section.

Another aortic occlusion device 2J is now described in connection with FIGS. 28–30 wherein the same or similar reference numbers describe the same or similar structure. The aortic occlusion device 2J includes a balloon 160 having a first, smaller section 162 and a second, larger section 164. The first section 162 minimizes the amount of space that the balloon 160 occupies in the aorta to maximize space in the aorta for performing aortic valve procedures and proximal anastomoses in coronary artery bypass procedures. The second section 164 stabilizes the first section 162 so that the first section 162 remains stable in the aorta. If the balloon 160 was discoid, for example, the balloon 160 may become unstable in the aorta and partially flip to one side or the other. Flipping or distortion of the balloon 160 can prevent full occlusion of the aorta which would allow warm, oxygenated blood to reach the patient's coronary arteries and possibly start the patient's heart beating before the procedure is completed.

Figures 29, 30:
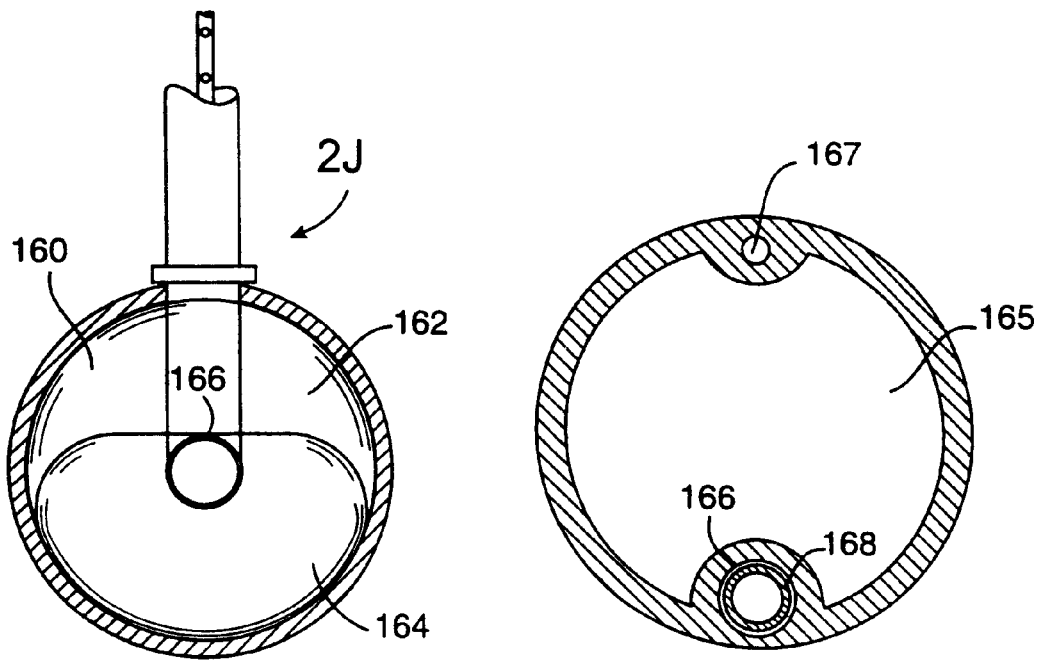
FIG. 29 is an end view of the balloon along line II—II of FIG. 28.
FIG. 30 is a cross-sectional view of FIG. 28 along line III—III.

Referring to the end view of FIG. 29, the second section 164 expands to a semi-circular profile with a top portion 166 of the second section 164 bonded to the shaft. The second section 164 preferably extends about 180 degrees around the cannula, however, the second section 164 may extend anywhere between 90 degrees and 230 degrees around the cannula shaft.

A cross-sectional view of the aortic occlusion device 2J is shown in FIG. 30. The aortic occlusion device 2J is preferably wire-reinforced in the manner described above, however, the aortic occlusion device 2J may be manufactured in any other suitable manner. The aortic occlusion device 2J includes a lumen 165 having an outlet to return oxygenated blood to the patient. The aortic occlusion device 2J also has a lumen 166 to deliver cardioplegic fluid and vent the aorta and a lumen 167 to inflate the balloon 160. The lumen 166 may also receive a vent catheter 168 which passes into the ascending aorta to vent blood from the ascending aorta as described above.

Figure 31:
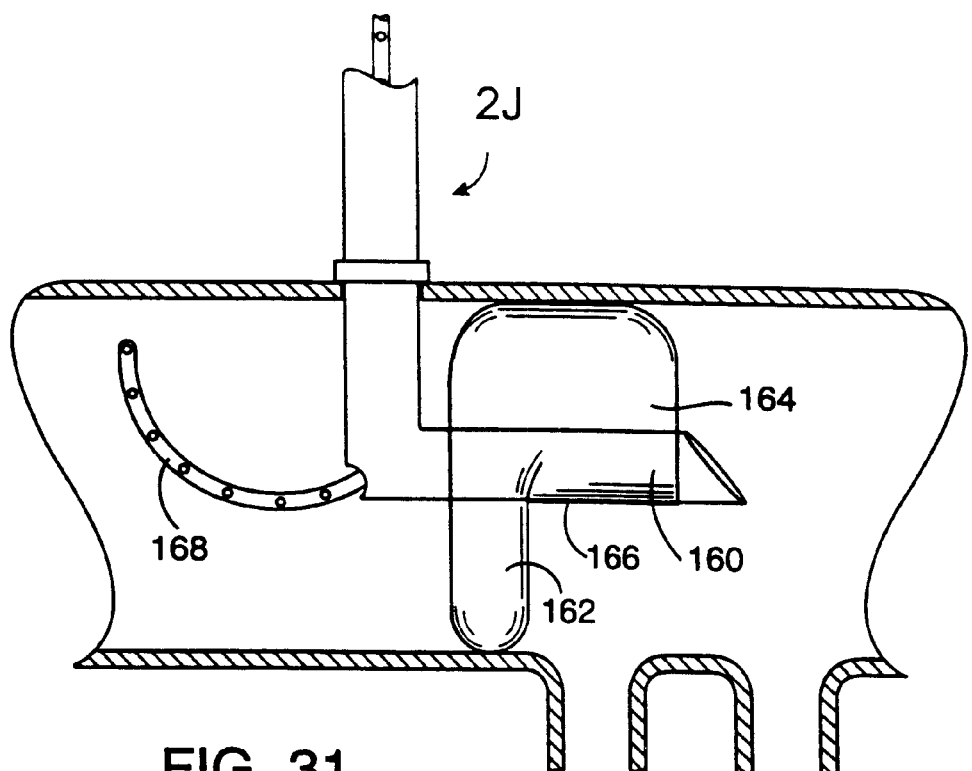
FIG. 31 shows the balloon of FIG. 28 having a different orientation on the shaft.
Figure 32:
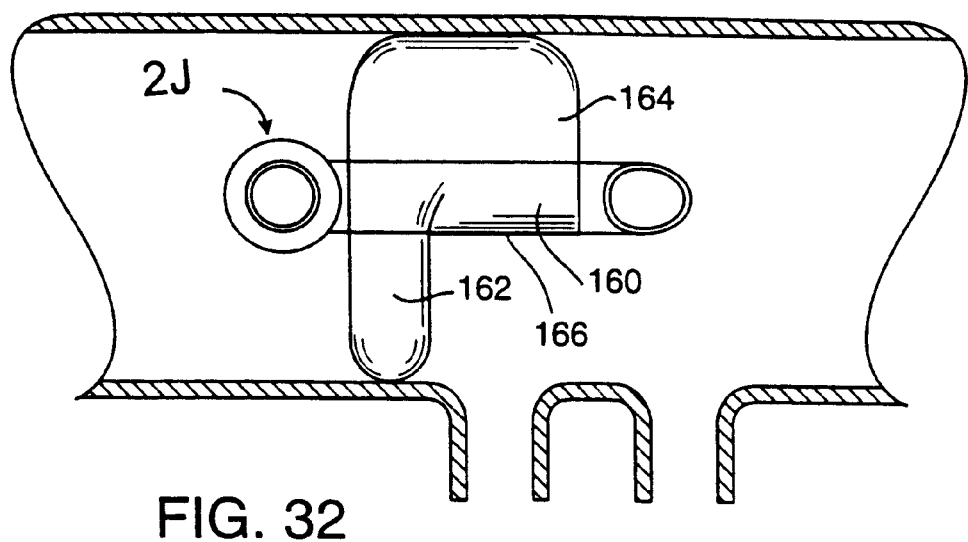
FIG. 32 shows yet another orientation for the balloon of FIG. 28.
Figure 33:
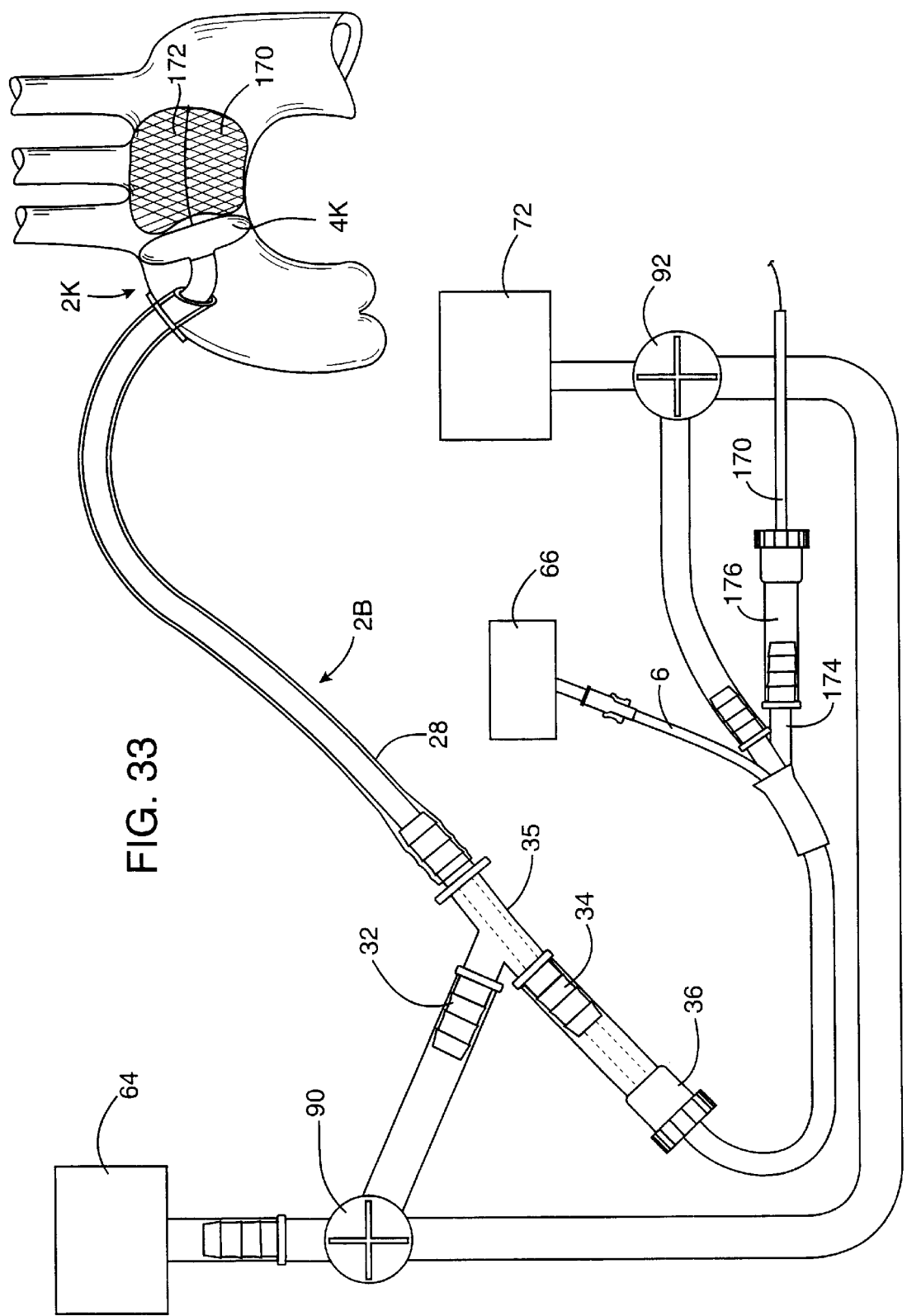
FIG. 33 shows a discoid occluding member supported by a stabilizer having an open structure which permits blood flow to the head and neck vessels.

The first and second sections 162, 164 may be positioned around the aortic occlusion device 2J in any orientation depending upon the angle and location that the cannula 2J is introduced into the aorta. The second section 164 is preferably positioned diametrically opposite the head and neck vessels so that the head and neck vessels are not blocked. FIG. 31 shows the first and second sections 162, 164 switched for use when the cannula is introduced from an inferior location. FIGS. 32 and 33 show yet another embodiment where the first and second sections 162, 164 are on opposite sides of the cannula. The aortic occlusion device 2J may, of course, take any of the forms described herein. For example, the orientation of the device 2J may be reversed so that blood passes through the lumen 166 and cardioplegic fluid is delivered through the lumen 165. The aortic occlusion device 2J may also be configured with the separate arterial cannula 28 (FIG. 12) rather than having the lumen 165 integrated into the device 2J.

Referring to FIG. 34, another aortic occlusion device 2K is shown wherein like or similar reference numbers refer to like or similar structure. The aortic occlusion device 2K has a thin, discoid occluding member 4K, which is preferably a balloon, stabilized and supported by a stabilizer 170. As mentioned above, the discoid occluding member 4K may be unstable in the aorta which can cause a portion of the occluding member to flip or otherwise distort thereby preventing full occlusion of the aorta. The stabilizer 170 supports and stabilizes the occluding member 4K thereby preventing the discoid occluding member 4K from flipping or distorting. The stabilizer 170 is positioned adjacent the occluding member to engage and contact the occluding member 4K.

The stabilizer 170 is preferably an open mesh 172 when in the expanded condition which permits blood flow to the head and neck vessels. An advantage of the stabilizer 170 is that the discoid occluding member 4K can be moved closer to the head and neck vessels to provide more room in the aorta to perform surgical procedures. Although the stabilizer 170 preferably has a woven or mesh structure, the stabilizer 170 may also be a perforated tube or an expanding basket or cone without departing from the scope of the invention.

The device 2K has the arterial cannula 2B and the aortic occlusion device 2B described above and the system may, of course, have any of the other suitable cannula and/or catheter configuration. The aortic occlusion device 2K includes another y-arm connector 174 having a hemostasis valve 176 which receives the stabilizer 170. The stabilizer 170 is preferably independent of the shaft supporting the occluding member 4K but may also be integrally formed with the shaft to which the occluding member 4K is attached.

Referring to FIGS. 35 and 36, the stabilizer 170 includes a shaft 178 having a passageway 180 which receives a wire 182 which is pulled to move the stabilizer 170 to the expanded condition of FIG. 36. A proximal end 184 of the mesh 172 is attached to a distal end 186 of the shaft 178 and a distal end 188 of the mesh 172 is attached to the wire 182. The stabilizer 170 is naturally biased to the contracted position of FIG. 35 so that the stabilizer 170 is collapsed by simply releasing tension on the wire 182. The mesh 172 is preferably made of stainless steel wire or a plastic braid, although any suitable material may be used.

Although the method described above positions the aortic occlusion device through an opening separate from the opening through which the surgeon operates, the cannula and aortic occlusion device 2 may also be introduced through the same opening through which the surgeon operates. The choice of opening location, number and size are a matter of surgical choice depending upon patient anatomy, the medical procedure being performed, surgeon preference and the particular embodiment of the invention being used. Furthermore, the devices described herein may have application in other parts of the heart and in other parts of the body. Thus, the description of the specific procedure described above is merely an example and other surgical methods may be used with the devices and methods of the present invention.

What is claimed is:

1. An arterial cannula assembly for perfusion of blood into a patient, comprising:

an arterial cannula having a blood flow lumen;

an introducer removably received in the blood flow lumen, the introducer comprising a cutting element, the cutting element being movable from a retracted position to an extended position beyond a distal end of the introducer; and a catheter slidably received by the arterial cannula;

the arterial cannula having a first shape when the introducer is positioned in the blood flow lumen, the arterial cannula having a second shape when the introducer is removed from the blood flow lumen.

2. An arterial cannula assembly, comprising:

an elongate shaft having a first section, a second section, a proximal end and a distal end, the first section extending from the proximal end toward the second section and the second section extending from the first section to the distal end, the second section extending for a length of between 2–6 cm from the distal end, the first section and the second sections forming an angle therebetween of about 110 to 140 degrees;

a lumen passing through the elongate shaft, the blood flow lumen having an outlet; and a stabilizing ring positioned around the second section of the elongate shaft, the stabilizing element forming an angle of 45 to 85 degrees with respect the second section.

3. The arterial cannula assembly of claim 2 further comprising:

an introducer removably positioned in the blood flow lumen, the introducer extending beyond the distal end of the elongate shaft when positioned in the blood flow lumen.

4. The arterial cannula assembly of claim 2, wherein:

the introducer has a cutting element which is movable from an extended position to a retracted position, the cutting element extending beyond a distal end of the introducer when in the extended position.

5. The arterial cannula assembly of claim 2 further comprising:

a y-arm connector coupled to the proximal end of the elongate shaft, the y-arm connector having a first arm and a second arm, the first arm being fluidly coupled to the blood flow lumen, the second arm having a hemostasis valve for receiving a catheter.

6. The arterial cannula assembly of claim 5, further comprising:

an aortic occlusion catheter received by the second arm of the y-arm connector, the aortic occlusion catheter having an occluding member movable from a collapsed shape to an expanded shape.

* * * * *